(12) United States Patent
Campbell et al.

(10) Patent No.: US 7,576,121 B2
(45) Date of Patent: *Aug. 18, 2009

(54) PYRROLIDINE COMPOUNDS AND METHODS FOR SELECTIVE INHIBITION OF DIPEPTIDYL PEPTIDASE-IV

(75) Inventors: David Alan Campbell, San Diego, CA (US); David T. Winn, San Diego, CA (US); Juan Manuel Betancort, San Diego, CA (US)

(73) Assignee: Phenomix Corporation, San Diego, CA (US)

( * ) Notice: Subject to any disclaimer, the term of this patent is extended or adjusted under 35 U.S.C. 154(b) by 253 days.

This patent is subject to a terminal disclaimer.

(21) Appl. No.: 11/381,082

(22) Filed: May 1, 2006

(65) Prior Publication Data

US 2006/0258621 A1 Nov. 16, 2006

Related U.S. Application Data

(63) Continuation-in-part of application No. 10/514,575, filed as application No. PCT/US2004/37820 on Nov. 12, 2004.

(60) Provisional application No. 60/676,808, filed on May 2, 2005, provisional application No. 60/592,972, filed on Jul. 30, 2004, provisional application No. 60/557,011, filed on Mar. 25, 2004, provisional application No. 60/519,566, filed on Nov. 12, 2003.

(51) Int. Cl.
*A61K 31/4025* (2006.01)
*C07D 207/10* (2006.01)

(52) U.S. Cl. ...................... 514/422; 548/405
(58) Field of Classification Search ................ 548/405; 514/422

See application file for complete search history.

(56) References Cited

U.S. PATENT DOCUMENTS

| | | | |
|---|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,572,912 A | 2/1986 | Yoshioka et al. |
| 4,681,893 A | 7/1987 | Roth |
| 4,759,923 A | 7/1988 | Buntin et al. |
| 4,871,721 A | 10/1989 | Biller |
| 4,924,024 A | 5/1990 | Biller |
| 4,935,493 A | 6/1990 | Bachovchin et al. |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,447,954 A | 9/1995 | Gribble et al. |
| 5,462,928 A | 10/1995 | Bachovchin et al. |
| 5,488,064 A | 1/1996 | Sher |
| 5,491,134 A | 2/1996 | Sher et al. |
| 5,541,204 A | 7/1996 | Sher et al. |
| 5,574,017 A | 11/1996 | Gutheil |
| 5,594,016 A | 1/1997 | Ueno et al. |
| 5,595,872 A | 1/1997 | Wetterau, II et al. |
| 5,614,492 A | 3/1997 | Habener |
| 5,631,224 A | 5/1997 | Efendic et al. |
| 5,686,104 A | 11/1997 | Mills et al. |
| 5,712,279 A | 1/1998 | Biller et al. |
| 5,712,396 A | 1/1998 | Magnin et al. |
| 5,739,135 A | 4/1998 | Biller et al. |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,952,301 A | 9/1999 | Drucker |
| 5,952,322 A | 9/1999 | Hoover et al. |

(Continued)

FOREIGN PATENT DOCUMENTS

DE 19616486 A1 10/1997

(Continued)

OTHER PUBLICATIONS

Morissette et al. Advanced Drug Delivery Reviews 2004, 56, 275-300.*

(Continued)

*Primary Examiner*—Rebecca L Anderson
*Assistant Examiner*—Jason Nolan
(74) *Attorney, Agent, or Firm*—Schwegman, Lundberg & Woessner, P.A.

(57) ABSTRACT

The present invention is directed to pyrrolidinylaminoacetyl pyrrolidine boronic acid compounds that display selective, potent dipeptidyl peptidase IV (DPP-IV) inhibitory activity. These compounds are useful for the treatment of disorders that can be regulated or normalized via inhibition of DPP-IV including those characterized by impaired glycemic control such as Diabetes Mellitus and related conditions. The compounds can be administered alone or with another medicament that displays pharmacological activity for treatment of these and other diseases.

56 Claims, No Drawings

U.S. PATENT DOCUMENTS

| | | | |
|---|---|---|---|
| 5,962,440 | A | 10/1999 | Sulsky |
| 5,965,532 | A | 10/1999 | Bachovchin |
| 5,998,463 | A | 12/1999 | Hulin et al. |
| 6,011,155 | A | 1/2000 | Villhauer |
| 6,040,145 | A | 3/2000 | Huber et al. |
| 6,107,317 | A | 8/2000 | Villhauer |
| 6,110,949 | A | 8/2000 | Villhauer |
| 6,124,305 | A | 9/2000 | Villhauer |
| 6,166,063 | A | 12/2000 | Villhauer |
| 6,172,081 | B1 | 1/2001 | Damon |
| 6,258,597 | B1 | 7/2001 | Bachovchin et al. |
| 6,300,314 | B1 | 10/2001 | Wallner et al. |
| 6,303,661 | B1 | 10/2001 | Demuth et al. |
| 6,355,614 | B1 | 3/2002 | Wallner |
| 6,380,398 | B2 | 4/2002 | Kanstrup et al. |
| 6,395,767 | B2 | 5/2002 | Robl et al. |
| 6,432,969 | B1 | 8/2002 | Villhauer |
| 6,617,340 | B1 | 9/2003 | Villhauer |
| 6,989,402 | B1 | 1/2006 | Hangeland et al. |
| 7,317,109 | B2 | 1/2008 | Campbell et al. |
| 2003/0100563 | A1 | 5/2003 | Edmondson et al. |
| 2003/0153509 | A1 | 8/2003 | Bachovchin et al. |
| 2006/0264400 | A1 | 11/2006 | Campbell et al. |
| 2006/0264401 | A1 | 11/2006 | Campbell et al. |
| 2006/0276410 | A1 | 12/2006 | Campbell et al. |
| 2007/0185061 | A1 | 8/2007 | Campbell |
| 2007/0299036 | A1 | 12/2007 | Campbell et al. |
| 2008/0182995 | A1 | 7/2008 | Campbell et al. |

FOREIGN PATENT DOCUMENTS

| | | |
|---|---|---|
| EP | 0818448 B1 | 1/1998 |
| EP | 0896538 B1 | 2/1999 |
| EP | 0978279 A1 | 2/2000 |
| EP | 1041068 B1 | 4/2004 |
| KR | 20060121170 | 11/2006 |
| WO | WO-89/03223 A1 | 4/1989 |
| WO | WO-8903223 A1 | 4/1989 |
| WO | WO-91/16339 A1 | 10/1991 |
| WO | WO-93/08259 A2 | 4/1993 |
| WO | WO-93/10127 A1 | 5/1993 |
| WO | WO-95/11689 A1 | 5/1995 |
| WO | WO-95/15309 A1 | 6/1995 |
| WO | WO-96/39384 A1 | 12/1996 |
| WO | WO-96/39385 A1 | 12/1996 |
| WO | WO-97/12613 A1 | 4/1997 |
| WO | WO-97/12615 A1 | 4/1997 |
| WO | WO-97/21993 A2 | 6/1997 |
| WO | WO-98/00439 A2 | 1/1998 |
| WO | WO-98/19998 A2 | 5/1998 |
| WO | WO-98/50046 A1 | 11/1998 |
| WO | WO-99/00353 A1 | 1/1999 |
| WO | WO-99/03850 A1 | 1/1999 |
| WO | WO-99/26659 A1 | 6/1999 |
| WO | WO-99/38501 A2 | 8/1999 |
| WO | WO-99/43663 A1 | 9/1999 |
| WO | WO-00/34241 A1 | 6/2000 |
| WO | WO-00/38722 A1 | 7/2000 |
| WO | WO-00/47206 A1 | 8/2000 |
| WO | WO-03/045228 A2 | 6/2003 |
| WO | WO-03/045977 A2 | 6/2003 |
| WO | WO-2004/004661 A2 | 1/2004 |
| WO | WO-2004044661 A3 | 5/2004 |
| WO | WO-2005/047297 A1 | 5/2005 |
| WO | WO-2005075426 A1 | 8/2005 |
| WO | WO-2006040625 A1 | 4/2006 |

OTHER PUBLICATIONS

Kirkpatrick, P. Nature Reviews Drug Discovery Jul. 2002, 1, 486-7.*

"Avasimibe: Treatment of Lipoprotein Disorders, ACAT Inhibitor", *Drugs of the Future* 24(1), (1999), 9-15.

"International Search Report and Written Opinion for PTC Application No. PTC/US04/37820", (Mar. 10, 2005), 9 pgs.

Bachovchin, W. W., et al., "Inhibition of IgA1 Proteinases from *Neisseria gonorrhoeae* and *Hemophilus influenzae* by Peptide Prolyl Boronic Acids", *Journal of Biological Chemistry.* 265(7), (Mar. 5, 1990), 3738-3743.

Balkan, B., et al., "Improved Insulin Secretion and Oral Glucose Tolerance after In Vivo Inhibition of DPP-IV in Obese Zucker Rats", *Diabetologia*, Suppl. 40, A131 Abstract, (1977),1 page.

Biller, S. A., et al., "Communications to the Editor: Isoprenoid (Phosphinylmethyl)phosphonates as Inhibitors of Squalene Synthetase", *Journal of Medicinal Chemistry*, 31(10), (Oct. 1988), 1869-1871.

Biller, S. A., "Squalene Synthase Inhibitors", *Current Pharmaceutical Design*, 2(1), (1996), 1-40.

Corey, E. J., "Application of Unreactive Analogs of Terpenoid Pyrophosphates to Studies of Multistep Biosynthesis. Demonstration That "Presqualene Pyrophosphate" Is An Essential Intermediate on the Path to Squalene", *Journal of the American Chemical Society*, 98(5), (1976), 1291-1293.

Coutts, S. J., "Structure-Activity Relationships of Boronic Acid Inhibitors of Dipeptidyl Peptidase IV. 1. Variation of the $P_2$ Position of $X_{aa}$-boroPro Dipeptides", *J. Med. Chem.* 39(10), (1996), 2087-2094.

Coutts, S. J., et al., "Two Efficient Methods for the Cleavage of Pinanediol boronate Esters Yielding the Free Boronic Acids", *Tetrahedron Letters*, 35(29), (1994),5109-5112.

Deacon, C. F., et al., "Both Subcutaneously and Intravenously Administered Glucagon-Like Peptide I are Rapidly Degraded From the $NH_2$-Terminus in Type II Diabetic Patients and in Healthy Subjects", *Diabetes*, 44(9), Retrieved from the Internet: <http://gateway.ut.ovid.com.floyd.lib.umn.edu/gw2/ovidweb.cgi>, (1995), 1126-1131, (11 pgs.).

Deacon, C. F., et al., "Dipeptidyl Peptidase IV Inhibition as an Approach to the Treatment and Prevention of Type 2 Diabetes: a Historical Perspective", *Biochemical and Biophysical Research Communications 294*, (2002), 1-4.

Demuth, H.-U. , et al., "Rebuttal to Deacon and Holst: "Metformin Effects on Dipeptidyl Peptidase IV Degradation of Glucagon-like Peptide-1" Versus "Dipeptidyl Peptidase Inhibition as an Approach to the Treatment and Prevention of Type 2 Diabetes: a Historical Perspective"", *Biochemical and Biophysical Research Communications 296*, (2002), 229-232.

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", *Cardiovascular Drug Reviews*, 16(1), (1998), 16-30.

Hara, S. , "Ileal $Na^+$/blle Acid Cotransporter Inhibitors", *Drugs of the Future*, 24(4), (1999), 425-430.

Hinke, S. A., et al., "Metformin Effects on Dipeptidyl-Peptidase IV Degradation of Glucagon-like Peptide-1", *Biochemical and Biophysical Research Communications 291*, (2002), 1302-1308.

Holst, Jens J., et al., "Perspectives in Diabetes: Inhibition of the Activity of Dipeptidyl-Peptidase IV as a Treatment for Type 2 Diabetes", *Diabetes*, vol. 47, From the Department of Medical Physiology, University of Copenhagen, Copenhagen, Denmark, (Nov. 1998), 1663-1670.

Kelly, T. A., et al., "Immunosuppresive Boronic Acid Dipeptides Correlation Between Conformation and Activity", *Journal of the American Chemical Society*, 115(26), (1993), 12637-12638.

Krause, B. R., "ACAT Inhibitors: Physiologic Mechanisms for Hypolipidemic and Anti-Atherosclerotic Activities in Experimental Animals", *Inflammation: Mediators and Pathways*, Ruffolo, Jr., et al., Editors, published by CRC Press, Boca Raton, FL, (1995), 173-198.

Kubota, T., et al., "Dipeptidyl Peptidase IV (DP IV) Activity in Serum and on Lymphocytes of MRL/Mp-*lpr/lpr* Mice Correlates With Disease Onset", *Clin Exp Immunol 96*, (1994), 292-296.

McClard, R W., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", *J. Am. Chem. Soc.*, vol. 109, (1987), 5544-5545.

Murakami, K., "A Novel Insulin Sensitizer Acts as a Coligand for Peroxisome Proliferation—Activated Receptor-α (PPAR-α) and PPAR-γ—Effect on PPAR-α Activation on Abnormal Lipid Metabolism in Liver of Zucker Fatty Rats", *Diabetes*, vol. 47, (Dec. 1998), 1841-1847.

Nicolosi, R. J., et al., "The ACAT Inhibitor, CI-1011 is Effective in the Prevention and Regression of Aortic Fatty Streak Area in Hamsters", *Atherosclerosis 137*, (1998),77-85.

Ortiz De Montellano, P. R., "Inhibition of Squalene Synthetase by Farnesyl Pyrophosphate Analogues", *Journal of Medicinal Chemistry*, 20(2), (1977), 243-249.

Pauly, R. P., et al., "Inhibition of Dipeptidyl Peptidase IV (DP IV) in Rat Results in Improved Glucose Tolerance", *Abstracts from the 11th International Symposium on Regulatory Peptides*, (1996), p. 148.

Rosenblum, S. B., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", *J. Med. Chem. 41*, (1998), 973-980.

Salisbury, B. G., "Hypocholesterolemic Activity of a Novel Inhibitor of Cholesterol Absorption, SCH 48461", *Atherosclerosis 115*, (1995), 45-63.

Sendobry, S. M., "Attenuation of Diet-Induced Atherosclerosis in Rabbits with a Highly Selective 15-lipoxygenase Inhibitor Lacking Significant Antioxidant Properties", *British Journal of Pharmacology 120*, (1997), 1199-1206.

Sliskovic, D. R., "ACAT Inhibitors: Potential Anti-atherosclerotic Agents", *Current Medicinal Chemistry*, 1(3), (1994), 204-225.

Smith, C., "RP 73163: A Bioavailable Alkysulphinyl-Diphenylimidazole ACAT Inhibitor", *Bioorganic & Medicinal Chemistry Letters*, 6(1), (1996), 47-50.

Stout, D. M., et al., "Inhibitors of Acyl-CoA: Cholesterol O-Acyl Transferase (ACAT) as Hypocholesterolemic Agents. 6. The First Water-Soluble ACAT Inhibitor With Lipid-Regulating Activity", *Chemtracts-Organic Chemistry*, vol. 8, (1995), 359-362.

Tanaka, S., et al., "Suppression of Arthritis by the Inhibitors of Dipeptidyl Peptidase IV", *International Journal of Immunopharmacology*, 19(1), (1997), 15-24.

Tanaka, S., et al., "Suppression of Arthritis by the Inhibitors of Dipeptidyl PeptidaseIV", *Ensho—Japanese Journal of Inflammation*, 18(3), (1998), 199-202.

U.S. Appl. No. 10/514,575, Preliminary Amendment filed Nov. 6, 2006, 19 pgs.

U.S. Appl. No. 10/514,575, Supplemental Preliminary Amendment Nov. 13, 2006, 21 pgs.

International Application Serial No. PCT/US04/37820, International Search Report mailed Mar. 10, 2005, 5 pgs.

International Application Serial No. PCT/US04/37820, Written Opinion mailed Mar. 10, 2005, 4 pgs.

"Point Therapeutics", http://www.pther.com, http://web.archive.org/web/20070827113729/http://www.pther.com/, Jun. 10, 2008.

Augustyns, K., et al., "The unique properties of dipeptidyl-peptidase IV (DPP IV / CD26) and the therapeutic potential of DDP IV inhibitors", *Curr Med Chem.*, 6(4), (Apr. 1999), 311-27.

Balkan, B., et al., "Inhibition of dipeptidyl peptidase IV with NVP-DPP728 increases plasma GLP-1 (7-36 amide) concentrations and improves oral glucose tolerance in obese Zucker rats.", *Diabetologia*, 42(11), (Nov. 1999), 1324-31.

Chen, W. T, "DPPIV and seprase in cancer invasion and angiogenesis.", *Adv Exp Med Biol.*, 524, (2003), 197-203.

Conarello, S. L, et al., "Mice lacking dipeptidyl peptidase IV are protected against obesity and insulin resistance.", *Proc Natl Acad Sci U S A.*, 100(11), (May 27, 2003), 6825-30.

Dang, N. H, et al., "CD26: an expanding role in immune regulation and cancer.", *Histol Histopathol.*, 17(4), (Oct. 2002), 1213-26.

Hughes, T. E, et al., "NVP-DPP728 (1-[[[2-[(5-cyanopyridin-2-yl)amino]ethyl]amino]acetyl]-2-cyano-(S)- pyrrolidine), a slow-binding inhibitor of dipeptidyl peptidase IV.", *Biochemistry*, 38(36), (Sep. 7, 1999), 11597-603.

Lambeir, A M, et al., "Kinetic investigation of chemokine truncation by CD26/dipetidyl peptidase IV reveals a striking selectivity within the chemokine family", *J Biol Chem.*, 276(32), (Aug. 10, 2001), 29839-45.

Marighetto, A, et al., "Further evidence for a dissociation between different forms of mnemonic expressions in a mouse model of age-related cognitive decline: effects of tacrine and S 17092, a novel prolyl endopeptidase inhibitor.", *Learn mem.*, 7(3), (May-Jun. 2000), 159-69.

Mentlein, R, "Dipeptidyl-peptidase IV (CD26)—role in the inactivation of regulatory peptides.", *Regul Pept.*, 85(1), (Nov. 30, 1999), 9-24.

Morain, P., et al., "Pharmacodynamic and pharmacokinetic profile of S 17092, a new orally active prolyl endopeptidase inhibitor, in elderly healthy volunteers. A phase I study.", *Br J Clin Pharmacol.*, 50(4), (Oct. 2000), 350-9.

Pederson, R. A, et al., "Improved glucose tolerance in Zucker fatty rats by oral administration of the dipeptidyl peptidase IV inhibitor isoleucine thiazolidide.", *Diabetes*, 47(8), (Aug. 1998), 1253-8.

Pospisilik, J. A, et al., "Dipeptidyl peptidase IV inhibitor treatment stimulates beta-cell survival and islet neogenesis in streptozotocin-induced diabetic rats.", *Diabetes*, 52(3), (Mar. 2003), 741-50.

Sedo, A., et al., "Dipeptidyl peptidase IV-like molecules: homologous proteins or homologous activities?", *Biochim Biophys Acta.*, 1550(2), (Dec. 17, 2001), 107-16.

Sudre, B., et al., "Chronic inhibition of circulating dipeptidyl peptidase IV by FE 999011 delays the occurrence of diabetes in male zucker diabetic fatty rats.", *Diabetes*, 51(5), (May 2002), 1461-9.

Umemura, K., et al., "Pharmacokinetics and safety of Z-321, a novel specific orally active prolyl endopeptidase inhibitor, in healthy male volunteers.", *J Clin Pharmacol.*, 39(5), (May 1999), 462-70.

Van Damme, J., et al., "The role of CD26/DPP IV in chemokine processing.", *Chem Immunol.*, 72, (1999), 42-56.

Vanhoof, G., et al., "Proline motifs in peptides and their biological processing.", *FASEB J.*, 9(9), (Jun. 1995), 736-44.

"U.S. Appl. No. 10/514,575, Response filed Sep. 17, 2008 to Restriction Requirement mailed Aug. 19, 2008", 21 pgs.

"U.S. Appl. No. 10/514,575, Restriction Requirement mailed Aug. 19, 2008", 11 pgs.

"U.S. Appl. No. 11/381,085, Non-Final Office Action mailed Aug. 1, 2007", 9 pgs.

"U.S. Appl. No. 11/381,085, Notice of Allowance mailed Oct. 11, 2007", 4 pgs.

"U.S. Appl. No. 11/381,085, Response filed May 2, 2007 to Restriction Requirement mailed Apr. 2, 2007", 13 pgs.

"U.S. Appl. No. 11/381,085, Response filed Sep. 13, 2007 to Non-Final Office Action mailed Aug. 1, 2007", 9 pgs.

"U.S. Appl. No. 11/381,085, Restriction Requirement mailed Apr. 2, 2007", 12 pgs.

"U.S. Appl. No. 11/381,090, Response filed Mar. 17, 2008 to Restriction Requirement mailed Feb. 19, 2008", 3 p.

"U.S. Appl. No. 11/381,090, Response filed Sep. 23, 2008 to Non Final Office Action mailed Jun. 26, 2008", 25 pgs.

"U.S. Appl. No. 11/381,090, Restriction Requirement mailed Feb. 19, 2008", 12 pgs.

"U.S. Appl. No. 11/381,090 Non-Final Office Action mailed Jun. 26, 2008", OARN, 18 Pgs.

"U.S. Appl. No. 11/556,944, Preliminary Amendment mailed Jul. 15, 2008", 9 pgs.

"Chilean Application Serial No. 1034-06, Office Action mailed Oct. 6, 2008", 10 pgs.

"International Application Serial No. 04810839.3, Non-Final Office Action mailed Jul. 18, 2007", 4 pgs.

"International Application Serial No. 04810839.3, Supplemental European Search Report mailed Dec. 13, 2006", 3 pgs.

"International Application Serial No. 06015708.8, Non-Final Office Action mailed Aug. 17, 2007", 1 pgs.

"International Application Serial No. 06015708.8-2177, Extended European Search Report mailed Dec. 13, 2006", 16 pgs.

"International Application Serial No. 2,545,311, Non-Final Office Action mailed May 10, 2007", 1 pg.

"International Application Serial No. 200603077-9, Non-Final Office Action mailed Mar. 24, 2008", 5 pgs.

"International Application Serial No. 200603077-9, Non-Final Office Action mailed May 29, 2007", 5 pgs.

"International Application Serial No. 200603077-9, Response filed Aug. 27, 2007 to Non-Final Office Action mailed May 29, 2007", 45 pgs.

"Korean Application Serial No. 10-2006-7011419, OAR-MISC mailed May 16, 2008", 10 pgs.

Coutts, M. J., et al., "Structure-activity relationships of boronic acid inhibitors of dipeptidyl peptidase IV. 1. Variation of the P2 position of Xaa-boroPro dipeptides.", *J Med Chem.*, 39(10), (May 10, 1996), 2087-94.

Flentke, G. R., et al., "Inhibition of dipeptidyl aminopeptidase IV (DP-IV) by Xaa-boroPro dipeptides and use of there inhibitors to examine the role of DP-IV in T-cell function", *PNAS, USA*, 88,, abstract obtained from CAPLUS database, accession No. 114:205351, (1991), 2 pgs.

U.S. Appl. No. 10/514,575, Non-Final Office Action mailed Dec. 29, 2008, 34 pgs.

U.S. Appl. No. 10/514,575, Response filed Mar. 23, 2009 to Non Final Office Action mailed Dec. 29, 2008, 31 pgs.

U.S. Appl. No. 11/381,090, Final Office Action mailed Dec. 22, 2008, 17 pgs.

U.S. Appl. No. 11/381,090, Response filed Mar. 20, 2009 to Final Office Action mailed Dec. 22, 2008, 13 pgs.

\* cited by examiner

PYRROLIDINE COMPOUNDS AND METHODS FOR SELECTIVE INHIBITION OF DIPEPTIDYL PEPTIDASE-IV

CROSS REFERENCE TO RELATED APPLICATIONS

This application is a continuation-in-part of U.S. application Ser. No. 10/514,575, filed on Oct. 27, 2005, which is a national stage application of PCT/US04/037820, filed Nov. 12, 2004 which claims priority to U.S. provisional application No. 60/519,566, filed on Nov. 12, 2003, U.S. provisional application No. 60/557,011, filed on Mar. 25, 2004, and U.S. provisional application No. 60/592,972, filed on Jul. 30, 2004. This application is also a continuation-in-part of U.S. Application No. 60/676,808, filed on May 2, 2005. These applications are incorporated herein by reference.

FIELD OF THE INVENTION

The present invention relates to pyrrolidinylaminoacetyl pyrrolidine boronic acid compounds and their use as selective inhibitors of post-proline/alanine cleaving amino-dipeptidases, particularly dipeptidyl peptidase-IV (DPP-IV). The invention also relates to methodology for employing such pyrrolidine compounds, alone or with another medicament, to treat a DPP-IV-related disease, including but not limited to disorders characterized by impaired glycemic control, especially Diabetes Mellitus and related conditions. Thus, the invention has applications in the medicinal, chemical, pharmacological, and medical fields.

BACKGROUND OF THE INVENTION

DPP-IV is a serine protease that belongs to a group of post-proline/alanine cleaving amino-dipeptidases. DPP-IV catalyzes the release of an N-terminal dipeptide of any configuration from proteins, and preferably, the dipeptide contains an N-terminal penultimate proline or alanine.

The physiological role of DPP-IV has not been established fully. It is believed to play an important role in regulatory peptide metabolism, which, among other things, controls various physiological functions including but not limited to glycemic control and insulin sensitivity. In particular, DPP-IV has been implicated in the control of glucose metabolism because its substrates include the insulinotropic hormones, glucagon like peptide-1 (GLP-1) and gastric inhibitory peptide (GIP), which are inactivated by removal of their two N-terminal amino acids.

In vivo administration of synthetic inhibitors of DPP-IV prevents N-terminal degradation of insulinotropic hormones including GLP-1 and GIP resulting in higher plasma concentrations of these hormones, increased insulin secretion and improved glucose tolerance. Therefore, such inhibitors have been proposed for the treatment of patients with impaired glycemic control such as Diabetes Mellitus and related conditions This proposal has significant difficulties, however. Additional dipeptide cleaving amino-dipeptidases have been discovered including DPP-VII, DPP-VIII, DPP-IX, and fibroblast activation protein (FAP), which can have substrate and inhibitor specificity similar to DPP-IV. The precise physiological role of each of these dipeptide cleaving enzymes is not well defined. But their propensity to cleave N-terminus dipeptides from proteins in general indicates that these amino-dipeptidases are involved in many physiological cycles. Thus, the difficulty concerning inhibitors of DPP-IV is that they can also affect the other members of the enzyme group. The evidence indicates that, for example, other inhibitors of DPP-IV, which also inhibit the other amino-dipeptidases such as DPP-VIII, will cause toxic effects in animals.

Accordingly, a need exists for compounds that are useful for inhibiting DPP-IV without an adverse event profile that precludes chronic administration.

SUMMARY OF THE INVENTION

The present invention is directed to selective DPP-IV inhibitors and methods of use that are effective in treating conditions that may be regulated or normalized by inhibition of DPP-IV. More particularly, the invention is directed to pyrrolidinylaminoacetyl pyrrolidine boronic acid compounds. These compounds are useful at effective doses for treatment of malconditions associated with DPP-IV activity and are selective inhibitors of DPP-IV.

The pyrrolidinylaminoacetyl boronic acid compounds of the invention (hereinafter the pyrrolidine compound(s) of the invention) have a structure represented in part by Formula I.

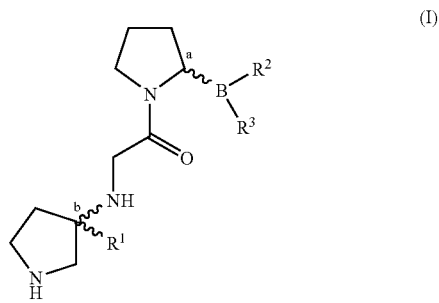

(I)

The substituents and bond designations of formula I include: $R^1$ which may be a substituted or unsubstituted alkyl, alkenyl, aralkyl, cycloalkyl, cycloalkylalkyl, cycloalkenyl, cycloalkenylalkyl, heterocyclyl, or heterocyclylalkyl group; and $R^2$ and $R^3$ independently or together are —OH, —O$^-$M$^+$ wherein M$^+$ is a cation, a hydroxyl bearing a boronic acid protecting group, or a group capable of being hydrolyzed to a hydroxyl group in an aqueous solution at physiological pH or in biological fluids. The wavy lines at asymmetric carbons $C^a$ and $C^b$ independently indicate for each asymmetric carbon an R configuration, an S configuration, or a mixture of both configurations such that all stereoisomers and all stereomeric mixtures are included. Also included within the scope of the pyrrolidine compounds of the invention are cyclic isomers thereof, any pharmaceutically acceptable salts thereof, any prodrugs thereof, and any solvates thereof. Preferred pyrrolidine compounds of the invention include compounds wherein $R^1$ is a substituted or unsubstituted ($C_{3-20}$)alkyl, ($C_{2-8}$)alkenyl, ($C_6$-$C_{15}$)aralkyl, ($C_3$-$C_{12}$)cycloalkyl, ($C_4$-$C_{20}$)cycloalkylalkyl, ($C_3$-$C_{12}$)cycloalkenyl, ($C_4$-$C_{20}$)cycloalkenylalkyl, ($C_3$-$C_{20}$ with N, O and/or S) heterocyclyl, or ($C_4$-$C_{20}$ with N, O and/or S) heterocyclylalkyl group. Especially preferred pyrrolidine compounds of the invention include those having the $R^1$ groups: alkyl, aralkyl, cycloalkyl, cycloalkylalkyl, heterocyclyl and heterocyclylalkyl. The pyrrolidine compounds of the invention having $R^1$ as methyl or ethyl are disclosed and claimed in copending U.S. application entitled "Methyl and Ethyl Substituted Pyrrolidine Compounds and Methods for Selective Inhibition of Dipeptidyl Peptidase-IV" filed on same date herewith.

A pyrrolidine compound of the invention may exist in either of two forms, the linear form represented by formula I above and the cyclic isomer form represented by formula V below.

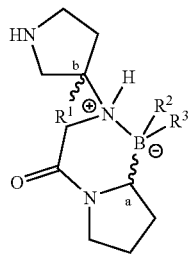

V

The cyclic isomer form and the linear form are in thermodynamic equilibrium when in solution. The equilibrium shifts depending upon pH. Thus, the predominance of one form over the other in solution depends upon the pH so that at acidic pH, the linear isomer predominates, while at basic pH, the cyclic isomer predominates. The linear and cyclic isomers are also stable such that either form may be isolated as a solid. The isolated cyclic isomer may function as a prodrug.

The invention also is directed to a pharmaceutical composition containing a pyrrolidine compound of the invention and a pharmaceutical carrier. The pharmaceutical composition may be formulated to be dosed by any administrative route including but not limited to parenteral injection, oral, buccal, rectal and the like.

The invention is also directed to a method of treating a malcondition that can be regulated or normalized via inhibition of DPP-IV. The method involves administration of an effective amount of a pyrrolidine compound of the invention, such as would be present in a pharmaceutical composition of the invention, to mammals, especially humans, to affect a malcondition that can be regulated or normalized via inhibition of DPP-IV. Preferably, an effective amount of a pyrrolidine compound of the invention exhibits lower toxicity than do non-selective inhibitors of DPP-IV, particularly in comparison to boronic acid inhibitors of DPP-IV that also display inhibition of other DPP enzymes and FAP. Therefore, the invention is directed to methods for selectively inhibiting DPP-IV involving, for example, administering to a patient in need of such treatment a therapeutically effective amount of a pyrrolidine compound of the invention.

The invention further is directed to a pharmaceutical combination of a pyrrolidine compound of the invention and one or more other medicaments that are useful for treatment of a malcondition that can be regulated or normalized via inhibition of DPP-IV. Such malconditions are associated with impairments in glycemic control especially Diabetes Mellitus and related conditions. A pharmaceutical combination may be formulated according to the invention as a pharmaceutical composition.

The invention is also directed to a process for preparing a pyrrolidine compound of the invention, a method for preparing a pharmaceutical composition of the invention, and the use of a pyrrolidine compound of the invention in a method for the preparation of a medicament for treating a malcondition that can be regulated or normalized via inhibition of DPP-IV.

DEFINITIONS

The term "absolute configuration" in connection with an asymmetric carbon is determined by considering the tetrahedral shape of the asymmetric carbon bonds, assigning a priority of 1 through 4 to each of the groups bound to the asymmetric carbon with the group having the highest atomic number having the first priority. If the tetrahedron is viewed from a side remote from group 4, an R absolute configuration is assigned when groups 1-3 are in a clockwise arrangement and an S absolute configuration is assigned when groups 1-3 are in a counterclockwise arrangement.

The term "and/or," as used herein, means one member of the named group or any combination thereof.

The term "asymmetric carbon" means a carbon atom covalently bound to four different groups.

The term "beta cell degeneration" is intended to mean loss of beta cell function, beta cell dysfunction, and death of beta cells, such as necrosis or apoptosis of beta cells.

The term "Diabetes Mellitus and related conditions" refers to Type 1 diabetes, Type 2 diabetes, gestational diabetes, MODY, impaired glucose tolerance, impaired fasting glucose, hyperglycemia, impaired glucose metabolism, insulin resistance, obesity, diabetic complications, and the like.

The term "diabetic complications" refers to conditions, diseases and maladies associated with diabetes including retinopathies, neuropathies, nephropathies, cardiomyopathies, dermopathies, arthrosclerosis, coronary artery disease and other known complications of diabetes.

The term "diastereomer" means one member of a group of two or more stereoisomers having at least two asymmetric carbons such that these stereoisomers are not mirror images of each other.

The terms "DPP-VII, DPP-VIII, DPP-IX and FAP" mean respectively amino dipeptidyl peptidase VII, VIII, IX and fibroblast activation protein. The DPP enzymes cleave dipeptide moieties at the N-terminus of their protein or oligopeptide substrates. In particular, the term "DPP-IV" denotes dipeptidyl peptidase IV (EC 3.4.14.5; DPP-IV), also known as "CD-26." DPP-IV preferentially cleaves a dipeptide from the N terminus of a polypeptide chain containing a proline or alanine residue in the penultimate position.

The term "enantiomer" means one member of a pair of stereoisomers having the same molecular structure and at least one asymmetric carbon such that the stereoisomers of the pair are the mirror images of each other. If the enantiomer contains two or more asymmetric carbons, the enantiomeric pair will have opposing asymmetry at each asymmetric carbon.

The term "group that can be hydrolyzed to a hydroxyl" as used herein refers to an ester group formed from the combination of an aliphatic or aromatic alcohol or diol and a boronic acid.

The term "inhibitor" (and its corresponding verb and gerund) means a compound that will reversibly, irreversibly or temporarily interact with an enzyme so as to reduce, modify, slow down or block its enzymatic activity upon its normal substrate. The interaction may occur within or at the enzymatic site or at an allosteric site associated with the enzyme.

The term "N-protecting group" or "N-protected" as used herein refers to those groups intended to protect the N-terminus of an amino acid or peptide or to protect an amino group against undesirable reactions during synthetic procedures.

Commonly used N-protecting groups are disclosed in T. W. Greene, P. G. Wuts, "Protective Groups In Organic Synthesis, 3$^{rd}$ Ed." (John Wiley & Sons, New York (1999)), which is hereby incorporated by reference. N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

The term "optically active" means an organic compound containing at least one asymmetric carbon such that a solution of the organic compound will rotate plane polarized light.

The term "optically active mixture" means a mixture of optically active compounds in solution that will rotate plane polarized light. The optically active mixture may be a mixture of diastereomers or an unequal mixture of enantiomers.

The term "pharmaceutical salt" means a salt with an inorganic base, organic base (including basic amino acids), inorganic acid, and organic acid (including acidic amino acids). Included as examples of inorganic bases are alkali metals such as lithium, sodium or potassium; alkaline earth metals such as calcium and magnesium or aluminum; and ammonia. Included as examples of organic bases are trimethylamine, triethylamine, pyridine, picoline, ethanolamine, diethanolamine, and triethanolamine. Included as examples of inorganic acids are the instant invention includes, for example, hydrohalogen acids such as hydrochloric acid, hydroboric acid, nitric acid, sulfuric acid, and phosphoric acid. Included as examples of organic acids are mono, di and tri carboxylic or sulfonic acids of 1 to 20 carbons, optionally containing 1 to 6 hydroxyl groups. Included as examples of basic amino acids are arginine, lysine and ornithine. Included as examples of acidic amino acids are aspartic acid and glutamic acid. Further examples of pharmaceutically acceptable salts include the pharmaceutically acceptable salts listed in Journal of Pharmaceutical Science, 66, 2 (1977) which are known to the skilled artisan.

The term "prodrug" means a pharmaceutically acceptable compound that will convert to the active ingredient or an active metabolite thereof upon administration of the prodrug to a living organism, preferably a mammal, more preferably a human. The conversion may occur by enzymatic action, chemical hydrolysis, oxidation, reduction or any other in vivo physiological process for chemical or biochemical reaction.

The term "racemic mixture" means an enantiomeric pair of equal proportions such that they cancel each other's rotation of plane polarized light.

A singular term such as "a pyrrolidine compound of the invention" includes the plural such as the various species of the pyrrolidine compounds of the invention as well as mixtures thereof. A plural term such as "pyrrolidine compounds of the invention" includes the individual species as well as the plural indicated by this term, and also mixtures thereof.

The term "selectivity ratio" refers to the $IC_{50}$ value generated in a biochemical assay measuring inhibition of DPP-IV compared to the $IC_{50}$ value generated in a biochemical assay measuring inhibition of another DPP family member (e.g. DPP-VII, DPP-VIII, DPP-IX or FAP) whereby the ratio is obtained by dividing the $IC_{50}$ value of DPP-VII, DPP-VIII, DPP-IX or FAP by the $IC_{50}$ value for DPP-IV.

The term "solvate" means a solid, crystalline form of a compound which also incorporates molecules of a solvent into the crystal structure. Organic solvents as well as water are included. Another description of a water solvate is a hydrate or hydrated form.

The term "stereoisomer" means one of the absolute configurations of a single organic molecule having at least one asymmetric carbon. Included within the definition of a stereoisomer are enantiomers and diastereomers. One stereoisomer has one absolute configuration about each of the asymmetric carbons of the organic molecule. An organic molecule with one asymmetric carbon presents two stereoisomers. An organic molecule with two asymmetric carbons presents four stereoisomers. An organic molecule with three asymmetric carbons presents eight stereoisomers. Projecting plane polarized light through a solution containing one stereoisomer will cause rotation of the polarized plane.

The term "stereomeric mixture" means a mixture of two or more stereoisomers and includes enantiomers, diastereomers and combinations thereof. The stereomeric mixture may or may not be optically active.

The term "stereomeric purity" at a given percentage means that the designated stereoisomer predominates at that given percentage in a mixture of stereoisomers.

In general, "substituted" refers to a group as defined below in which one or more bonds to a hydrogen atom contained therein are replaced by a bond to non-hydrogen or non-carbon atoms such as, but not limited to, a halogen (i.e., F, Cl, Br, and I); an oxygen atom in groups such as hydroxyl groups, alkoxy groups, aryloxy groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, hydroxylamines, N-oxides, imides, urethanes, hydrazides, azides, amidines, guanidines, and enamines; and other heteroatoms in various other groups. Substituted alkyl, alkenyl, alkynyl, cycloalkyl, and cycloalkenyl groups as well as other substituted groups also include groups in which one or more bonds to a carbon(s) or hydrogen(s) atom is replaced by one or more bonds to a heteroatom such as, but not limited to, oxygen in carbonyl (oxo), carboxyl, and ester groups; nitrogen in imines, oximes, hydrazones, and nitriles.

$(C_3-C_{20})$ alkyl groups include, with exceptions, straight chain and branched alkyl groups having from 1 to about 20 carbon atoms, and typically from 1 to 12 carbons or, in some embodiments, from 1 to 8 carbon atoms. Examples of straight chain alkyl groups include those with from 3 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. Representative substituted alkyl groups may be substituted one or more times with any of the groups listed above, for example, amino, hydroxy, cyano, carboxy, nitro, thio, alkoxy, and halogen groups.

($C_3$-$C_{12}$) cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups farther include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which may be substituted with, for example, amino, hydroxy, cyano, carboxy, nitro, thio, alkoxy, and halogen groups.

($C_4$-$C_{20}$) cycloalkylalkyl groups are alkyl groups as defined above in which a hydrogen or carbon bond of an alkyl group is replaced with a bond to a cycloalkyl group as defined above.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halogen groups, bonded to one of the ring members. Rather, groups such as tolyl are referred to as substituted aryl groups. Representative substituted aryl groups may be mono-substituted or substituted more than once, such as, but not limited to, 2-, 3-, 4-, 5-, or 6-substituted phenyl or naphthyl groups, which may be substituted with groups such as those listed above.

($C_6$-$C_{15}$) aralkyl groups are alkyl groups as defined above in which a hydrogen or carbon bond of an alkyl group is replaced with a bond to an aryl group as defined above. Representative aralkyl groups include benzyl groups and fused (cycloalkylaryl)alkyl groups such as 4-ethyl-indanyl.

($C_3$-$C_{20}$ with N, O and/or S) heterocyclyl groups include aromatic and non-aromatic ring compounds containing 3 or more ring members, of which, one or more is a heteroatom such as, but not limited to, N, O, and S. In some embodiments, heterocyclyl groups include 3 to 20 ring members, whereas other such groups have 3 to 15 ring members. The phrase "heterocyclyl group" includes fused ring species including those comprising fused aromatic and non-aromatic groups. The phrase also includes polycyclic ring systems containing a heteroatom such as, but not limited to, quinuclidyl. However, the phrase does not include heterocyclyl groups that have other groups, such as alkyl or halogen groups, bonded to one of the ring members. Rather, these are referred to as "substituted heterocyclyl groups". Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups may be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups". Representative substituted heteroaryl groups may be substituted one or more times with groups such as those listed above.

($C_4$-$C_{20}$ with N, O and/or S) heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroaralkyl groups are alkyl groups as defined above in which a hydrogen or carbon bond of an alkyl group is replaced with a bond to a heteroaryl group as defined above.

Substituted aryl, substituted heterocyclyl and substituted heteroaryl also include rings and fused ring systems in which a bond to a hydrogen atom is replaced with a bond to a carbon atom. Therefore, substituted aryl, substituted heterocyclyl and substituted heteroaryl groups may also be substituted with alkyl, alkenyl, and alkynyl groups as defined above.

The term "alkoxy", and "($C_{1-6}$)alkoxy", alone or in combination, refer to an oxygen atom connected to an alkyl group as defined above or having 1-6 carbon atoms, respectively. Examples of linear alkoxy groups include but are not limited to methoxy, ethoxy, propoxy, butoxy, pentoxy, hexoxy, and the like. Examples of branched alkoxy include but are not limited to isopropoxy, sec-butoxy, tert-butoxy, isopentoxy, isohexoxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl. Examples include but are not limited to phenoxy, naphthyloxy, and benzyloxy.

The term "alkanoyl", alone or as part of another group, refers to alkyl linked to a carbonyl group.

The term "amido" includes C— and N-amido groups, i.e., —C(O)NR$^8$R$^9$, and —NR$^8$C(O)R$^9$ groups, respectively. R$^8$ and R$^9$ are independently hydrogen, or an alkyl, cycloalkyl, aryl, aralkyl, or heterocyclyl group as defined herein.

The term "carbamyl" includes N— and O-carbamyl groups, i.e., —NR$^{10}$C(O)OR$^{11}$ and —OC(O)NR$^{10}$R$^{11}$ groups, respectively. R$^{10}$ and R$^{11}$ are independently hydrogen, or an alkyl, cycloalkyl, aryl, aralkyl, or heterocyclyl group as defined herein.

The term "sulfonamido" includes S— and N-sulfonamide groups, i.e., —SO$_2$NR$^{12}$R$^{13}$ and —NR$^{12}$SO$_2$R$^{13}$ groups, respectively. R$^{12}$ and R$^{13}$ are independently hydrogen, or an alkyl, cycloalkyl, aryl, aralkyl, or heterocyclyl group as defined herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepine-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "alkylamino", "arylamino", or "arylalkylamino" alone or as part of another group includes any of the above alkyl, aryl or arylalkyl groups linked to a nitrogen atom.

Unless otherwise specifically stated, the definitions of terms for chemical groups, functional groups, moieties and chemical reactions described herein follow the definitions provided in such organic chemistry textbooks and treatises as "Basic Principles of Organic Chemistry", Roberts and Caserio, W.A. Benjamin & Co. New York, N.Y. 1965; "Advanced Organic Chemistry", 4$^{th}$ edition, Jerry March, Wiley Interscience, New York, N.Y. 1992; T. W. Greene, P. G. Wuts, "Protective Groups In Organic Synthesis, 3$^{rd}$ Ed." (John Wiley & Sons, New York (1999), and Hawley's Condensed Chemical Dictionary, 11$^{th}$ Ed., Sax and Lewis, Van Nostrand, Reinhold, New York, N.Y., 1987. Moreover, the definitions for stereochemical terms are based upon "Stereochemistry of Carbon Compounds", Ernest Eliel, McGraw-Hill publisher, New York, N.Y. 1962. The disclosures of these text books are incorporated herein by reference.

A further detailed description of the invention is given with reference to the following non-limiting examples.

DETAILED DESCRIPTION OF THE INVENTION

The pyrrolidinylaminoacetyl pyrrolidine boronic acid compounds of the invention (pyrrolidine compounds of the invention) have the linear and cyclic isomer structures depicted by formulas I and V above. All stereoisomers, stereomeric mixtures, pharmaceutically acceptable salts, solvates and prodrugs are included as embodiments of the "pyrrolidine compounds of the invention," (which is also termed "pyrrolidine compound" or "pyrrolidine compounds" herein). A pharmaceutical composition including a pyrrolidine compound of the invention and a pharmaceutically acceptable pharmaceutical carrier is an additional aspect of the invention. Also included is a pharmaceutical combination of a pyrrolidine compound of the invention and a second medicament known to be useful in the treatment of malconditions characterized by impaired glycemic control, especially Diabetes Mellitus and related conditions. A pharmaceutical combination may be formulated as a pharmaceutical composition of a pyrrolidine compound, a second medicament and a pharmaceutically acceptable carrier.

An embodiment of a pyrrolidine compound of the invention include a borate ester and a boronic acid group such that R$^2$ and R$^3$ of formulas I and V, independently or together, are —OH, —O$^-$M$^+$ wherein M$^+$ is a cation, a hydroxyl bearing a boronic acid protecting group, or a group capable of being hydrolyzed to a hydroxyl group in an aqueous solution at physiological pH or in biological fluids. When R$^2$ and R$^3$ are groups that can be hydrolyzed to hydroxyl, they may be formed from mono-alcohols and diols of 1 to 15 carbons and the alcohols and diols may be linear, branched, cyclic or aromatic, and may optionally be substituted with ester and/or amide groups. Examples include (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol.

Surprisingly, it has been discovered that pyrrolidine compounds of the invention display selectivity for DPP-IV relative to other dipeptidyl peptidase enzymes. By selectivity for DPP-IV it is meant that a pyrrolidine compound of the invention more strongly inhibits DPP-IV, than at least one closely related enzyme such as DPP-VII, DPP-VIII, DPP-IX and FAP. While not wishing to be bound by any theory, it is believed that this unexpected selectivity for DPP-IV results in an improved therapeutic profile with diminished side-effects for the pyrrolidine compound of the invention compared with other boronic acid inhibitors and compared to any other non-selective DPP-IV inhibitor. In particular it is believed that potent inhibition of DPP-VIII by other inhibitors correlates with the acute toxicity observed in animal studies. As detailed in the following Examples section, administering a compound with DPP-IV and DPP-VIII inhibitory activity to dogs leads to severe emesis and diarrhea. The same compound administered to some strains of rats resulted in death. The pyrrolidine compounds of the invention avoid significant inhibition of DPP-VIII and therefore avoid the toxicities observed in both dog and rat.

Synthesis of the Pyrrolidine Compounds of the Invention

The invention also relates to processes for preparing pyrrolidine compounds of the invention. As shown below and as described in the examples, a pyrrolidine compound of the invention is prepared by reacting a pyrrolidine, suitably protected with a standard protecting group such as Boc-, Fmoc-, Cbz- or the like, with sec-BuLi/TMEDA followed by a boron source such as $B(OCH_3)_3$, to provide the boronic ester derivative. Acid hydrolysis of the methyl esters with HCl provides the boronic acid intermediate 1. Reaction of 1 with (+) pinanediol, deprotection of the amino protecting group, and recrystallization provides the pinanediol ester 2 as an isomerically pure salt.

Intermediate 2 is useful for the synthesis of a pyrrolidine compound of the invention. For example, N-acylation of 2 with chloroacetyl chloride provides the α-chloro amide 3. Treatment of 3 with $Na_2CO_3$ and a pyrrolidinylamine, hydrolysis of the pinanediol boronic ester, and N-deprotection provides a pyrrolidine compound of the invention, 4.

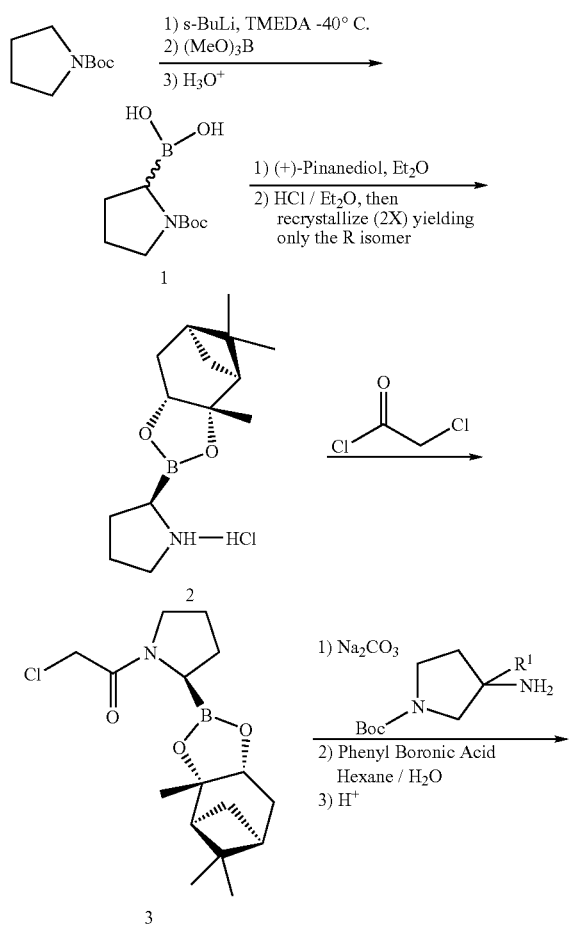

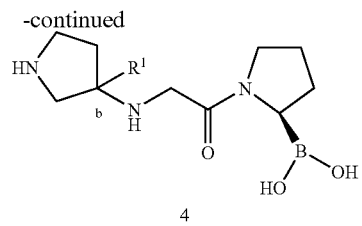

wherein $R^1$ is a substituted or unsubstituted ($C_{3-8}$) alkyl, ($C_{2-8}$) alkenyl, ($C_6$-$C_{15}$) aralkyl, ($C_3$-$C_{12}$) cycloalkyl, ($C_4$-$C_{20}$) cycloalkylalkyl, ($C_3$-$C_{12}$) cycloalkenyl, ($C_4$-$C_{20}$) cycloalkenylalkyl, ($C_3$-$C_{20}$ with N, O or S) heterocyclyl, or ($C_4$-$C_{20}$ with N, O or S) heterocyclylalkyl group. The S stereoisomer of 2 or a mixture of stereoisomers can be obtained by appropriate manipulation of the recrystallization step, which includes a resolution using an optically active pinanediol. Use of an R or S stereoisomer of the amino pyrrolidine reagent for reaction with 3, or use of a stereomeric mixture thereof will yield the desired stereochemistry at the $C^b$ asymmetric carbon as shown in structure 4.

Thus, another aspect of the invention provides a process for preparing a pyrrolidine compound of the invention including coupling a reactive compound of Formula II:

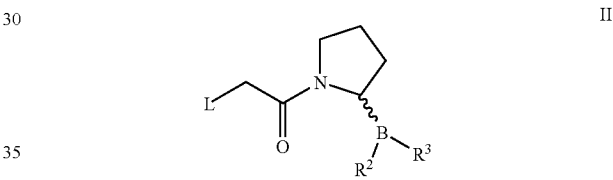

with a compound of Formula III:

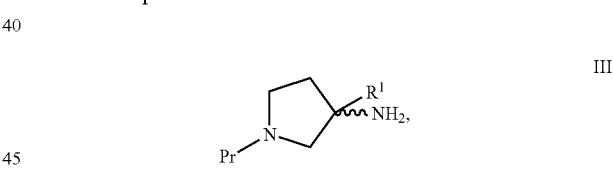

wherein L is a leaving group such as a halogen, mesylate, tosylate, triflate or the like; $R^2$ and $R^3$, independently or together, are —OH, —O$^-$M$^+$ wherein M$^+$ is a cation, a hydroxyl bearing a boronic acid protecting group, or a group capable of being hydrolyzed to a hydroxyl group in an aqueous solution at physiological pH or in biological fluids; Pr is an N-protecting group such as Boc, Cbz, Fmoc, benzyl or the like; and $R^1$ is a substituted or unsubstituted ($C_{3-8}$) alkyl, ($C_{2-8}$) alkenyl, ($C_6$-$C_{15}$) aralkyl, ($C_3$-$C_{12}$)cycloalkyl, ($C_4$-$C_{20}$)cycloalkylalkyl, ($C_3$-$C_{12}$) cycloalkenyl, ($C_4$-$C_{20}$)cycloalkenylalkyl, ($C_3$-$C_{20}$ with N, O or S)heterocyclyl, or ($C_4$-$C_{20}$ with N, O or S)heterocyclylalkyl group; to provide an ester derivative of a pyrrolidine compound of the invention. The resulting boronic ester derivative of the pyrrolidine compound of the invention may be deprotected to remove Pr and to recover the pyrrolidine compound of the invention as an ester, a free acid or as a salt. In some embodiments, L is halogen, including but not limited to Cl. In others $R^2$ and $R^3$ are each methoxy or together are pinanedioxy, e.g. (+)-pinanedioxy as in compound 3 above. In still others, Pr is Boc.

An alternative synthesis of a pyrrolidine compound of the invention is provided in U.S. patent application Ser. No. 60/704,380, filed Aug. 1, 2005 and entitled "Methods of Preparing Heterocyclic Boronic Acids and Derivatives Thereof."

The pyrrolidine compounds of the invention may be formed as pharmaceutically acceptable salts. A pharmaceutical salt may be obtained as the direct product of compound synthesis. In the alternative, a free base may be dissolved in a suitable solvent containing the appropriate acid (or vice versa), and the salt isolated by evaporating the solvent or otherwise separating the salt and solvent. The processes for forming pharmaceutically acceptable salts from amine compounds such as the pyrrolidine compounds of the invention are well-known in the art. See, for example, "The Practice of Medicinal Chemistry, Second Edition", by Camille G. Wermuth, Academic Press, New York, N.Y., 1996.

Pyrrolidine compounds of the invention may form solvates with standard low molecular weight solvents, including water to yield hydrates, using methods known to the skilled artisan. These processes for forming solvates are also well-known in the art. See, for example, "The Practice of Medicinal Chemistry" cited above.

It is to be understood that the invention extends to all of the stereoisomers of the pyrrolidine compounds, including enantiomers, diastereomers, as well as the racemates and stereoisomeric mixtures. The mixtures may or may not be optically active.

In some embodiments, pyrrolidine compounds of the invention may have an optical purity of at least about 55%, preferably 80%, more preferably 90 wt %, most preferably 98% or more of a single stereoisomer. In other embodiments, the pyrrolidine compounds are optically-enriched enantiomers. In still other embodiments, the pyrrolidine compounds are mixtures of stereoisomers including but not limited to unequal mixtures of enantiomers and/or mixtures of diastereomers.

Methods/Uses of the Pyrrolidine Compounds of the Invention

The methods of treatment and use of the pyrrolidine compounds of the invention are based upon inhibition of dipeptidyl peptidase-IV by contact of the enzyme dipeptidyl peptidase-IV with a pyrrolidine compound in any of its form as described above. The contact may be accomplished in vitro such as through a diagnostic test or a screening test, or in vivo through an appropriate administrative route as discussed below.

An in vivo method according to the invention involve a pyrrolidine compound of the invention in its role as a selective inhibitor of DPP-IV. For example, the invention provides a method of treatment of a mammal (such as a human) suffering from a malcondition that can be regulated or normalized via inhibition of DPP-IV such as any malcondition characterized by impaired glycemic control, especially Diabetes Mellitus and related conditions by administering an effective amount of a pyrrolidine compound of the invention to treat, control, ameliorate or prevent the malcondition. These malconditions are known to be the result, at least in part, of the presence, or altered activity, of peptides regulated by the enzyme DPP-IV, especially in the context of its physiological role in glycemic control. A method of the invention is accomplished by administering to the mammal (e.g., a human) an effective amount of a pyrrolidine compound of the invention. Treatment is affected by inhibition of DPP-IV. Administration is typically accomplished through use of a pharmaceutical composition containing a pyrrolidine compound of the invention.

The invention further includes a method for selectively inhibiting DPP-IV over related enzymes. In some embodiments of the methods for treatment, DPP-IV is inhibited by greater than 5-fold relative to one or more other dipeptidyl peptidases. In other embodiments, DPP-IV is inhibited by greater than 10-, 20-, or even 50-fold or more over other dipeptidyl peptidases. Exemplary other dipeptidyl peptidases include DPP-VII, DPP-VIII, DPP-IX, and FAP. For example, a pyrrolidine compound of the invention can selectively inhibits DPP-IV over dipeptidyl peptidase-VII, or DPP-IV over dipeptidyl peptidase-VIII, or DPP-IV over dipeptidyl peptidase-IX, or DPP-IV over fibroblast activation protein (FAP). In additional embodiments, the pyrrolidine compound of the invention selectively inhibits DPP-IV over dipeptidyl peptidase-VIII and fibroblast activation protein. In other embodiments, the pyrrolidine compound of the invention selectively inhibits DPP-IV over dipeptidyl peptidase-VII, dipeptidyl peptidase-VIII, and fibroblast activation protein. This selectivity applies to in vitro and to in vivo situations. In particular, it has been determined in an in vivo protocol study in humans that pyrrolidine compounds of the invention maintained selectivity for inhibition of DPP-IV over the other amino dipeptidyl peptidases. Preferably, the DPP-IV selectivity is shown relative to DPP-VIII.

For in vivo use as a DPP-IV inhibitor, a pyrrolidine compound of the invention may be formulated in any manner as described herein and administered in an effective amount to a patient (human) suffering from a malcondition that can be regulated or normalized by inhibition of DPP-IV, especially a malcondition characterized by impaired glycemic control, especially Diabetes Mellitus and related conditions. For example, the malcondition can be Type 1 diabetes, Type 2 diabetes, gestational diabetes, MODY, impaired glucose tolerance, impaired fasting glucose, hyperglycemia, impaired glucose metabolism, impaired glucose tolerance (IGT) and its progression to Type II diabetes, hyperinsulinemia, obesity, beta cell degeneration (in particular apoptosis of beta cells), the progression of non-insulin-requiring Type II diabetes to insulin requiring Type II diabetes; loss of the number and/or the size of beta cells in a mammalian subject, and diabetic complications such as retinopathy, neuropathy, nephropathy, cardiomyopathy, dermopathy, diabetes related infection, atherosclerosis, coronary artery disease, stroke and similar malconditions.

In other embodiments of methods of treatment according to the invention, insulin resistance is a component of the malcondition that can be regulated or normalized by inhibition of DPP-IV. For example, the malconditions can be impaired fasting glucose, impaired glucose tolerance, polycystic ovarian syndrome and the like. In yet other embodiments, the malcondition that can be regulated or normalized by inhibition of DPP-IV involves a decrease of islet neogenesis, β-cell survival, or insulin biosynthesis.

The administered dose of a pyrrolidine compound of the invention will be carefully adjusted according to age, weight and condition of the patient, as well as the route of administration, dosage form and regimen and the desired result. The ultimate choice of dosage, route and pharmaceutical formulation will be determined by the patient's attending physician, whose wisdom and judgment will guide this process. The dose for adults may range from about 0.5 to about 2,000 mg per day, preferably about 10 mg to about 1000 mg per day, more preferably about 50 mg to about 750 mg per day, which can be administered in a single dose or in the form of multiple doses given up to 4 times per day.

The uses of a pyrrolidine compound of the invention also include the manufacture of a medicine and a method of treatment using such a medicine in the form of a pharmaceutical composition.

Pharmaceutical Combinations and Their use in Treatment

A pyrrolidine compound of the invention may be combined with a second medicament to form a pharmaceutical combination of the invention. The second medicament is a known agent for treating, controlling, or preventing a malcondition that can be regulated or normalized via inhibition of DPP-IV. A malcondition treated by such combination is one that can be regulated or normalized via inhibition of DPP-IV and thus is the same as the one described above in connection with sole treatment using the pyrrolidone compounds of the invention.

The second medicament may include a therapeutically effective amount of a dipeptidyl peptidase-IV inhibitor other than the pyrrolidine compound of the invention. The second medicament preferably may be a known anti-diabetic agent including but not limited to an agent that increases insulin secretion, an agent that increases insulin sensitivity, an agent that reduces the uptake of sugar from the gastrointestinal track, an agent that enhances the effect of endogenous peptides or proteins that play a role in glycemic control, or an agent that acts a replacement therapy for endogenous peptides or proteins that have a known role in glycemic control. Such agents include but are not limited to glyburide (e.g. Micronase and Diabeta), glipizide (e.g. Glucotrol), nateglinide (e.g. Starlix), repaglinide (e.g. Prandin), metformin (e.g. Glucophage), rosiglitazone (e.g. Avandia), acarbose (e.g. Precose), miglitol (e.g. Glyset), exenatide (e.g. Byetta), and insulin (e.g. Humulin and Novolin). Additional exemplary agents include but are not limited to biguanides, chlorpropamide, a glucagon-like peptide-1 (GLP-1) or mimetic thereof such as LY315902 or LY307161, glimepiride, meglitinide, phenformin, pioglitazone, sulfonyl ureas, troglitazone, G1-262570, isaglitazone, JTT-501, NN-2344, L895645, YM-440, R-119702, AJ9677, KAD1129, APR-HO39242, GW-409544, KRP297, AC2993, Exendin-4, and NN2211. The chemical structures, trivial names and pharmacological studies of the foregoing compounds designated by letters and numbers are readily available from the web, for example, by entering the letter/number designation as a search term in the GOOGLE search web site.

A pyrrolidine compound of the invention may be used in combination with one or more second medicaments useful as antidiabetic agents (employed to treat diabetes and related diseases). The second medicament may be administered orally in the same dosage with the pyrrolidine compound of the invention, or in a separate oral dosage form. The pyrrolidine compounds of the invention and the second medicament may also be administered, for example by injection, separately, simultaneously or as a mixture.

The pharmaceutical combination of the invention can be formulated as a pharmaceutical composition of a pharmaceutically acceptable carrier along with a pyrrolidine compound of the invention and one or more second medicaments.

In the pharmaceutical combination of the invention, the pyrrolidine compound of the invention are typically present in a weight ratio to the second medicament of from about 0.01:1 to about 100:1, or preferentially from about 0.1:1 to about 5:1.

The use of a pyrrolidine compound of the invention in combination with one or more other antidiabetic agents may produce antihyperglycemic results greater than that possible from each of these antidiabetic agents alone. The use of a pyrrolidine compound of the invention in combination with one or more other antidiabetic agents may also produce a synergistic effect in that the antihyperglycemic result may be greater than the combined additive antihyperglycemic effects produced by these antidiabetic agents.

The effective amount of a second medicament formulated as a component of a pharmaceutical combination of the invention will follow the recommendations of the second medicament manufacturer, the judgment of the attending physician and will be guided by the protocols and administrative factors for amounts and dosing as indicated in the PHYSICIAN'S DESK REFERENCE (PDR).

The administered dose of a pyrrolidine compound of the invention within a pharmaceutical combination will be carefully adjusted according to age, weight and condition of the patient, as well as the route of administration, dosage form and regimen and the desired result. The ultimate choice of dosage, route and pharmaceutical formulation will determined by the patient's attending physician, whose wisdom and judgment will guide this process.

The compositions described above may be administered in the dosage forms as described above in single or divided doses of one to four times daily. It may be advisable to start a patient on a low dose combination and work up gradually to a high dose combination.

In a further embodiment of the pharmaceutical combinations of the invention, the second medicament can be known anti-obesity agents including but not limited to a beta 3 adrenergic agonist, a lipase inhibitor, a serotonin (and dopamine) reuptake inhibitor, a thyroid hormone receptor-beta agonist, an anorectic agent, a fatty acid oxidation upregulator, or a mixture of any two or more thereof. Suitable, known anti-obesity agents include orlistat, sibutramine, topiramate, axokine, dexamphetamine, phentermine, phenylpropanolamine, famoxin, mazindol, or a mixture of any two or more thereof. These anti-obesity agents may be employed in the same dosage form with a pyrrolidine compound of the invention or in different dosage forms, and the administrative dosages and regimens applied to the anti-obesity agents will follow the recommendations and guides generally known in the art and/or set out in the PDR.

In another embodiment of the pharmaceutical combinations of the invention, the second medicament may be an agent for treating polycystic ovary syndrome. The agent for polycystic ovary syndrome which may be optionally employed in combination with a pyrrolidine compound of the invention may be 1, 2, or more of gonadotropin releasing hormones (GnRH), leuprolide (Lupron®), Clomid®, Parlodel®, oral contraceptives or insulin sensitizers such as PPAR agonists, or other conventional agents for such use which may be employed in amounts specified in the PDR.

Pharmaceutical Compositions of the Invention

The invention includes a pharmaceutical composition containing a pyrrolidine compound of the invention, with or without another medicament as described above, in association with a pharmaceutical carrier. The pharmaceutical composition can be formulated with one or more carriers such as conventional solid or liquid vehicles or diluents and pharmaceutical additives of a type appropriate to the mode of desired administration. A pyrrolidine compound of the invention in a pharmaceutical composition can be administered to mammalian species, especially humans, an oral, buccal, rectal, pulmonary or similar route, for example, in the form of tablets, capsules, granules or powders. It can be administered by a parenteral route in the form of injectable preparations. It can be administered by a transdermal route either by a release patch for transdermal delivery or by electro-transport using an appropriate delivery device.

Pharmaceutical compositions containing a pyrrolidine compound of the invention can be prepared by conventional techniques, e.g., as described in Remington: The Science and Practice of Pharmacy, 19th Ed., 1995. The compositions may appear in conventional forms, for example capsules, tablets, aerosols, solutions, suspensions or topical applications.

A typical pharmaceutical composition includes a pyrrolidine compound of the invention formulated with a pharmaceutically acceptable carrier which may be an excipient or a diluent, or may be enclosed within a carrier which can be in the form of a capsule, sachet, tablet, paper or other container. In making the composition, conventional techniques for the preparation of pharmaceutical compositions may be used.

For example, a pyrrolidine compound of the invention will usually be mixed with a carrier, diluted by a carrier, or enclosed within a carrier which may be in the form of an ampoule, capsule, tablet, sachet, paper, or other container. When the carrier serves as a diluent, it may be solid, semi-solid, or liquid material that acts as a vehicle, excipient, or medium for the active compounds. The pyrrolidine compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax.

The formulations can be mixed with auxiliary agents which do not deleteriously react with the pyrrolidine compounds. Such additives can include wetting agents, emulsifying and suspending agents, salt for influencing osmotic pressure, buffers and/or coloring substances preserving agents, sweetening agents or flavoring agents. The pharmaceutical compositions can also be sterilized if desired.

The route of administration may be any route, which effectively transports the pyrrolidine compound of the invention to the appropriate or desired site of action, such as oral, nasal, pulmonary, buccal, rectal, subdermal, intradermal, transdermal or depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation cam be in the form of a syrup, emulsion, soft gelatin capsule or sterile injectable liquid such as an aqueous or non-aqueous liquid suspension or solution.

Injectable dosage forms generally include aqueous suspensions or oil suspensions, which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical composition may be a powder suitable for reconstitution with an appropriate solution as described above. Examples of these include, but are not limited to, freeze dried, rotary dried or spray dried powders, amorphous powders, granules, precipitates, or particulates. For injection, the pharmaceutical composition may optionally contain stabilizers, pH modifiers, surfactants, bioavailability modifiers and combinations of these. A pyrrolidine compound of the invention may be formulated for parenteral administration by injection such as by bolus injection or continuous infusion. A unit dosage form for injection may be in ampoules or in multi-dose containers.

A pharmaceutical composition of the invention may be designed to provide quick, sustained, or delayed release of the active ingredient after administration to the patient by employing procedures well known in the art. Thus, the pharmaceutical composition may also be formulated for controlled release or for slow release.

A pharmaceutical composition of the invention may include, for example, micelles or liposomes, or some other encapsulated form, or may be administered in an extended release form or an enteric coated form to provide a prolonged storage and/or delivery effect. Therefore, a pharmaceutical composition may be compressed into pellets or cylinders and implanted intramuscularly or subcutaneously as depot injections or as implants such as stents. Such implants may employ known inert materials such as silicones and biodegradable polymers, e.g., polylactide-polyglycolide. Examples of other biodegradable polymers include poly (orthoesters) and poly (anhydrides).

A pyrrolidine compound of the invention may be formulated as a sustained release implant or implantable material suitable for continuous administration over a significant period of time. Typical sustained release implants are formed from polymers of pharmaceutically acceptable, biodegradable polymers such as polymers and copolymers of lactic acid, lactide, glycolic acid, glycolide, caproic acid and caprolactone. The dose and amount of a pyrrolidine compound of the invention within the implant will be calculated to deliver the desired single dose blood level of pyrrolidine compound.

For nasal administration, a pharmaceutical composition may contain a pyrrolidine compound of the invention dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with a pyrrolidine compound of the invention dissolved in polyhydroxylated castor oil.

Tablets, dragees, or capsules having talc and/or a carbohydrate carrier, binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that may be prepared by conventional tabletting techniques may contain:

| Core: | |
|---|---|
| Pyrrolidine compound of the invention* | 300 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Adde |
| Coating: | |
| HPMC approx. | 9 mg |
| **Mywacett 9-40 T approx. | 0.9 mg |

*Pyrrolidine compound is formulated as free compound or salt thereof.
**Acylated monoglyceride used as plasticizer for film coating.

A typical capsule for oral administration contains a pyrrolidine compound of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of pyrrolidine compound of the invention into a vial, aseptically freeze-drying and sealing. For use, the contents of the vial are mixed with 2 mL of physiological saline, to produce an injectable preparation.

A pyrrolidine compound of the invention may be administered to a mammal, especially a human in need of such treatment, prevention, elimination, alleviation or amelioration of the various malconditions mentioned above. Such mammals include also animals, both domestic animals, e.g. household pets, farm animals, and non-domestic animals such as wildlife.

A pyrrolidine compound of the invention is effective over a wide dosage range. For example, in the treatment of adult humans, dosages from about 0.5 to about 2000 mg, preferably from about 10 mg to about 1000 mg, per day, more preferably about 50 to 750 mg per day can be used. A typical dosage is about 50 mg to about 750 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, a pyrrolidine compound of the invention is dispensed in unit dosage form including from about 0.5 to about 2000 mg of active ingredient together with a pharmaceutically acceptable carrier per unit dosage.

Usually, a dosage form suitable for oral, nasal, pulmonary or transdermal administration includes from about 0.5 mg to about 2000 mg, preferably from about 10 mg to about 1000 mg per day, more preferably from about 50 mg to about 750 mg of a pyrrolidine compound admixed with a pharmaceutically acceptable carrier or diluent.

A pharmaceutical combination of the invention may be formulated as a pharmaceutical composition employing all of the embodiments, carriers, route designs and the like described above for formulation of a pharmaceutical composition of a pyrrolidine compound alone.

The invention also encompasses prodrugs of a pyrrolidine compound of the invention which, on administration, undergo chemical conversion by metabolic processes before becoming active pharmacological substances. In general, such prodrugs will be functional derivatives of a pyrrolidine compound of the invention, which are readily convertible in vivo into the pyrrolidine compound of the invention. Conventional procedures for the selection and preparation of suitable prodrug derivatives are described, for example, in "Design of Prodrugs", ed. H. Bundgaard, Elsevier, 1985.

The invention also encompasses active metabolites of a pyrrolidine compound of the invention.

Thus, another aspect of the invention provides a pharmaceutical composition of a pyrrolidine compound of the invention, alone or in combination with another type antidiabetic agent and/or other type therapeutic agent.

Additional embodiments of the invention are represented by:
Pharmaceutical compositions including a pyrrolidine compound of the invention, as described above, together with at least one pharmaceutically acceptable carrier or diluent;
Methods of making a pharmaceutical composition of a pyrrolidine compound of the invention wherein the pharmaceutically acceptable carrier or diluent is suitable for oral administration;
Methods of making a pharmaceutical composition of a pyrrolidine compound of the invention suitable for oral administration further including the step of formulating the composition into a tablet or capsule;
Methods of making a pharmaceutical composition of a pyrrolidine compound of the invention wherein the pharmaceutically acceptable carrier or diluent is suitable for parenteral administration;
Methods of making a pharmaceutical composition of a pyrrolidine compound of the invention suitable for parenteral administration further including the step of lyophilizing the composition to form a lyophilized preparation.

DPP-IV inhibitory activity of a pyrrolidine compound of the invention can be determined by use of an in vitro assay system. The inhibition constant ($K_i$ or $IC_{50}$ values) for a DPP-IV inhibitor of the invention can be determined by the method described below.

A further detailed description of the invention is given with reference to the following non-limiting examples.

EXAMPLES

Example 1

Synthesis of Pyrrolidine Boronic Acid Compounds

Unless otherwise noted, materials were obtained from commercial suppliers and used without further purification. 1H NMR spectra were determined on a Bruker Avance 300 spectrometer. Chemical shifts are expressed in ppm downfield from internal tetramethylsilane. Mass spectra were obtained on a Finnigan LCQ mass spectrometer with ESI source.

THF and ethyl ether were distilled from sodium/benzophenone ketyl. Dichloromethane was dried by distillation from phosphorus pentoxide.

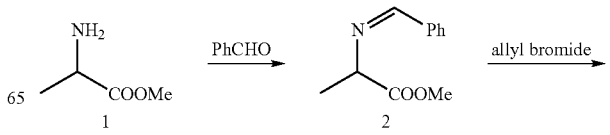

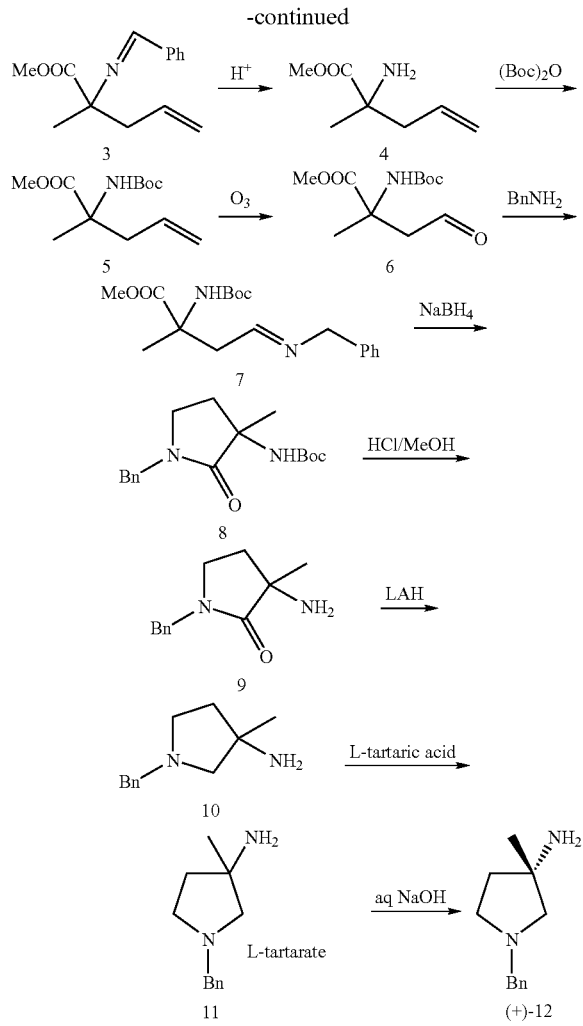

(m, 1H), 3.74 (s, 3H), 4.23-4.26 (m, 1H), 5.04-5.26 (m, 1H), 5.54-5.71 ( m, 1H); MS: 144 (M+1).

Preparation of compound 5: A solution of 4 (47 g, 0.33 mol) and Boc$_2$O (72 g, 0.33 mol) in THF (300 mL) was heated to reflux overnight. After concentration, the residue was purified by column chromatography on silica gel (PE: EA=10:1) to give compound 5 (50.1 g, 62.6%). $^1$H NMR (CDCl$_3$): δ 1.26 (m. 3H) 1.50 (s, 9H), 2.64-2.68 (m, 1H), 2.70-2.75 ( m, 1H), 3.74 (s, 3H), 5.04-5.28 (m, 2H), 5.41-5.48 (br, 1H), 5.54-5.70 (m, 1H); MS: 244 (M+1).

Preparation of compound 6: Through a solution of compound 5 (50.0 g, 0.21 mol) in CH$_2$Cl$_2$ (300 mL) at −78° C. was bubbled ozone until the solution turned gray-blue. Then PPh$_3$ (50.0 g, 0.21mol) was added slowly to quench the reaction. After concentration, the residue was purified by column chromatography on silica gel (PE: EA=10:1) to give compound 6 (27.1 g, 53.6%). $^1$H NMR (CDCl$_3$): δ0.84 (m, 3H), 1.51 (s, 9H), 2.91-2.96 (m, 1H,), 3.48-3.61 (m, 1H), 3.74 (s, 3H), 5.61 (br, 1H), 9.70 (s, 1H); MS: 246 (M+1).

Preparation of compound 7: To a solution of compound 6 (10.0 g, 40.8 mmol) in CH$_2$Cl$_2$ (100 mL) was added benzyl amine (4.36 g, 40.8 mmol) and MgSO$_4$ (6.8 g, 57 mmol). After stirring overnight, the resulting mixture was filtered and the filtrate was concentrated to afford compound 7 (12.6 g, 92.6%) as a brown oil. $^1$H NMR (CDCl$_3$): δ1.21 (t, 3H), 1.51 (s, 9H), 2.81-2.87 (m, 1H, ), 2.92-3.01 (m, 1H), 3.67 (s, 3H), 4.10-4.20 (m, 1H), 4.56 (m, 2H), 5.45-5.56 (br, 1H), 7.22-7.31 (m, 5H), 7.76 (br, 1H); MS: 335 (M+1).

Preparation of compound 8: To a solution of compound 7 (12.6 g, 37.7 mmol) in MeOH (200 mL) was added NaBH$_4$ (2.17 g, 45.25 mmol). After stirring 3 h at room temperature, the mixture was poured into water, extracted with ethyl acetate, and the combined organic phases were dried over Na$_2$SO$_4$ and concentrated to afford product 8 (9.1 g, 79.4%) as a brown oil. $^1$H NMR (CDCl$_3$): δ1.33 (s, 3H), 1.51 (s, 9H), 2.19-2.43 (m, 2H), 3.07-3.24 (m, 2H), 2.02-3.31 (m, 2H), 4.56-4.4 (d, 1H), 4.53-4.58 (d, 1H), 7.22-7.35 (m, 5H); MS: 305 (M+1).

Preparation of compound 9: A solution of 8 (9.1 g, 29.9 mmol) in anhydrous HCl/CH$_3$OH (200 mL) was stirred for 3 h. Then the solvent was evaporated to afford the HCl salt of 9 (6.1 g, 99.8%) as a brown oil. $^1$H NMR (CDCl$_3$): 1.36 (s, 3H), 2.05-2.20 (m, 2H), 3.14-3.25 (m, 2H), 4.41 (s, 2H), 7.23-7.35 (m, 5H), 8.66 (br, 1H); MS: 205 (M+1).

Preparation of compound 10: A solution of 9 (6.1 g, 29.9 mmol) in THF (20 mL) was added to a solution of LiAlH$_4$ (1.2 g, 32 mmol) in THF (10 mL) at room temperature. After stirring 2 h, water was added to quench this reaction. The resulting mixture was filtered through a pad of silica and the filtrate was evaporated to give crude product which was purified by flash chromatography on silica gel to give compound 10 (3.8 g, 66.9%) as a white solid. $^1$H NMR (CDCl$_3$): 1.50 (s, 3H), 1.82-1.85 (m, 1H), 2.04-2.13 (m, 1H), 2.39-2.50 (m, 2H), 2.85-2.99 (m, 2H), 3.59-3.70 (m, 2H), 7.20-7.36 (m, 5H); MS: 191 (M+1).

Preparation of compound 11: To a solution of 10 (6.5 g, 34.2 mmol) in CH$_3$OH (50 mL) was added a solution of L-tartaric acid (5.13 g, 34.5 mmol) in CH$_3$OH (50 mL). After being stirred for 2 h at room temperature, the resulting suspension was filtered and re-crystallized five times to get the desired compound 11 (1.1 g, 18.9%). $^1$H NMR (MeOD): 1.45 (s, 3H), 2.01-2.12 (m, 2H), 2.48 (d, 1H), 2.59-2.68 (m, 1H), 2.95 (d, 1H), 3.07-3.18 (m, 1H), 3.72 (d, 1H), 3.85 (d, 1H), 4.42 (s, 2H), 7.22-7.44 (m, 5H).

Preparation of compound 2: To a solution of 1 (100.0 g, 0.97 mol) in dichloromethane (1000 mL) was added triethyl amine (134 mL, 0.97 mol) dropwise. After being stirred for 30 min, benzaldehyde (102.8 g, 0.97 mol) was added, followed by the addition of MgSO$_4$ (232.0 g, 1.97 mol). The mixture was stirred overnight. After filtration, the filtrate was evaporated to give compound 2 (150.0 g, 81.1%). $^1$H NMR (CDCl$_3$): δ 1.52 (m, 3H), 3.74 (s, 3H), 4.15-4.17(m, 1H), 7.53-7.57 (m, 2H), 7.75-7.77 (m, 3H), 8.31 (s, 1H).

Preparation of compound 4: To a solution of t-BuOK (87.4 g, 0.78 mol) in THF (800 mL) at room temperature was added a solution of compound 2 (150.0 g, 0.78 mol) in THF (500 mL) dropwise. After stirring for 1 h, the solution of allyl bromide (94.4 g, 0.78 mol) in THF (400 mL) was added dropwise to the resulting mixture. After stirring overnight, the solvent was removed in vacuo and the residue extracted with ethyl acetate, washed with water and brine, dried over with anhydrous Na$_2$SO$_4$. The solvent was evaporated to give compound 3. To a solution of compound 3 in 450 mL ethyl acetate was added 6N HCl (400 mL). The mixture was stirred for one hour and then extracted with ethyl acetate, the aqueous phase was adjusted to pH 9-10 and extracted with ethyl acetate three times. The combined organic layers were dried and evaporated to afford compound 4 as a brown oil (70 g, 62.7%). $^1$H NMR (CDCl$_3$): δ1.26 (s, 3H), 2.51-2.61 (m, 1H), 2.63-2.69

Preparation of the compound (+)-12: A solution of 11 (1.1 g, 3.2 mmol) in 10 mL NaOH (2M) was stirred for 2 h at room temperature. The reaction was extracted with ethyl acetate, and the combined organic phases were dried over $Na_2SO_4$ and concentrated to afford product (+)-12 (600 mg, 97.7% ee ) (Table 1).

using (−)-7. (−)-7 was recovered from the mother liquor and isolated according to the preparation of compounds 33 to 35.

Example 2

Synthesis of Ethyl-substituted Pyrrolidine Boronic Acid Compounds

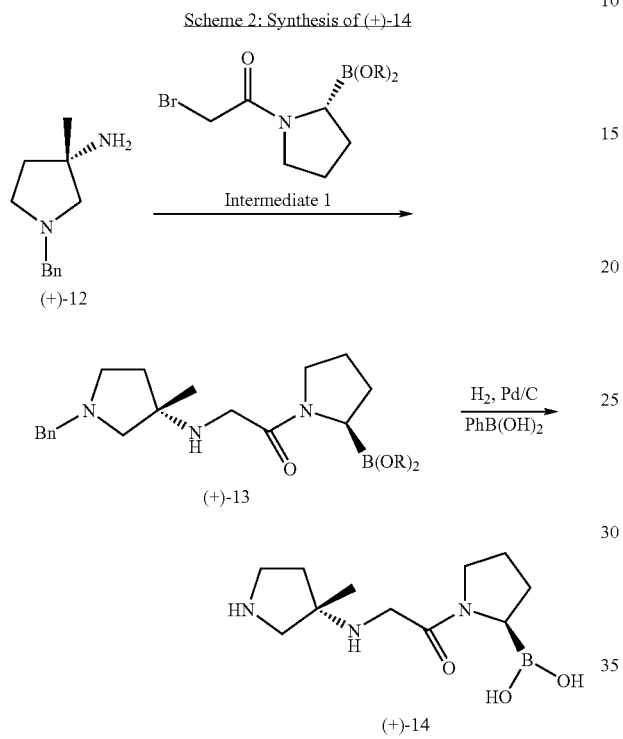

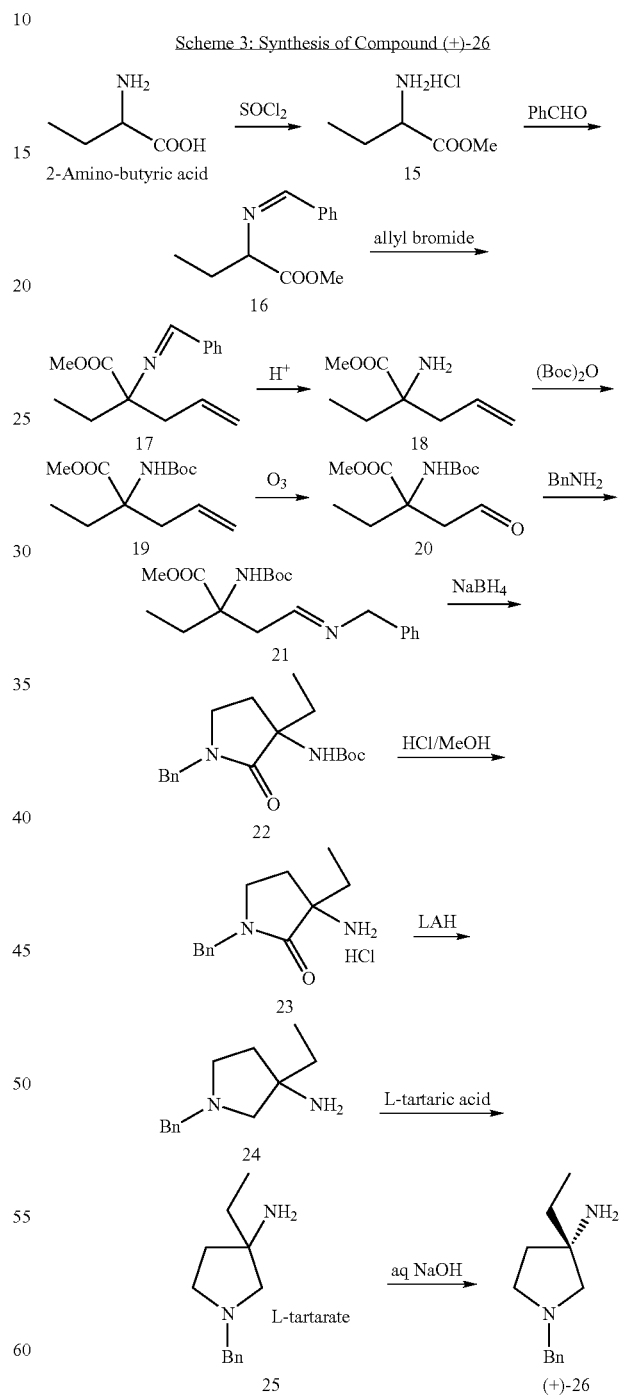

Preparation of compound (+)-13: To a solution of compound (+)-12 (100 mg, 0.52 mmol) in anhydrous $CH_3CN$ (10 ml) under argon was added Intermediate 1 (213.6 mg, 0.57 mmol) followed by the addition of $K_2CO_3$ (358 mg, 2.6 mmol). After stirring overnight, the mixture was filtered and the filtrate was evaporated and purified by p-HPLC to afford (+)-13 (30 mg, 12%). (M+1): 480.

Preparation of compound (+)-14: To the solution of compound (+)-13 (30 mg, 0.06 mmol) in MTBE (2 ml) was added 1N HCl (2 ml), followed by the addition of $PhB(OH)_2$ (9.2 mg, 0.075 mmol). After stirring for 2 h, 10 ml water was added before separation. The aqueous layer was washed with EA and $CH_2Cl_2$, and was used directly to the next step. (M+1): 346.

The solution of the above compound in THF (10 ml) was hydrogenated with $Pd(OH)_2/C$ at 20 psi $H_2$ After stirring 1 h, the mixture was filtered and the filtrate was lyophilized to afford the (+)-14 (8 mg, 52%). $^1H$ NMR (MeOD): δ1.62 ( s, 3H), 1.70-1.75 (m, 1H), 1.93-2.15 (m, 3H), 2.30-2.50 (m, 2H), 3.48-3.58 (m, 3H), 3.60-3.75 (m, 3H), 3.96-4.17 (m, 2H). (M+1): 256.

Preparation of Compound (−)-14: Following similar steps as outlined for compounds 12 to (+)-14 with the exception of Preparation of compound 15: To a solution of 2-aminobutyric acid (50 g, 0.48 mol) in MeOH (300 mL) at 0° C. was added thionyl chloride (66.7 g, 0.57 mol) dropwise. After stirring for 2 h, the reaction was concentrated and the precipitated solid was washed with diethyl ether to afford product 15 (63.0 g, 85.1%). $^1$H NMR (DMSO): δ0.85-0.92 (m, 3H), 1.86-2.0 (m, 2H), 3.73 (s, 3H), 3.91-4.12 (m, 1H), 8.40-8.54 (br, 3H).

Preparation of compound 16: To a solution of 15 (40.9 g, 0.27 mol) in dichloromethane (600 mL) was added dropwise triethyl amine (39 mL, 0.32 mol). After being stirred for 30 min, benzaldehyde (28.3 g, 0.27 mol) was added, followed by the addition of MgSO$_4$ (97.2 g, 0.81 mol). The mixture was stirred overnight. After filtration, the filtrate was evaporated to give compound 16 as a red oil (52.0 g, 94.9%). $^1$H NMR (CDCl$_3$): δ 0.88 (t, 3H), 1.86-2.0 (m, 2H), 3.68 (s, 3H), 3.83-3.88( m, 1H), 7.33-7.37 (m, 2H), 7.73-7.76 (m, 3H), 8.23 (s, 1H).

Preparation of compound 18: To a solution of t-BuOK (31.2 g, 0.28 mol) in THF (480 mL) at room temperature was added dropwise a solution of compound 16 (47.1 g, 0.23 mol) in THF (240 mL). After stirring for 1 h, a solution of allyl bromide (33.5 g, 0.28 mol) in THF (120 mL) was added dropwise to the mixture. After stirring overnight, the solvent was removed in vacuo and the residue was extracted with ethyl acetate, washed with water and brine, dried over with anhydrous Na$_2$SO$_4$. The solvent was evaporated to give the compound 17. To the solution of compound 17 in THF (150 mL), was added 6N HCl (200 mL) and the mixture was stirred for one hour. Then extracted with ethyl acetate, the aqueous phase was adjusted to pH=9-10 and extracted with ethyl acetate three times. The combined organic layers were dried and evaporated to afford compound 18 as a brown oil (34.5 g, 95.8%) $^1$H NMR: (CDCl$_3$): δ 0.82 (t, 3H), 1.49-1.51 (m, 1H), 1.61-1.63 (m, 1H), 2.13-3.25 (m, 1H), 2.42-2.59 (m, 1H), 3.68 (s, 3H), 5.17-5.27 (m, 2H), 5.62-5.78 (m, 1H); MS: 158 (M+1).

Preparation of compound 19: A solution of 18 (24.5 g, 0.15 mol) and Boc$_2$O (33 g, 0.15 mol) in THF (300 mL) was heated to reflux overnight. Then the solvent was evaporated and the residue was purified by column chromatography on silica gel (PE:EA=10:1) to give compound 19 (32.1 g, 84.4%) as a brown oil. $^1$H NMR (CDCl$_3$): δ0.77 (t, 3H) 1.50 (s, 9H), 1.85-1.95 (m, 1H), 2.17-2.29 (m, 1H), 2.44-2.51 (m, 1H), 2.95-3.05 (m, 1H), 3.68 (s, 3H), 5.01-5.06 (m, 2H), 5.38-5.46 (br, 1H), 5.55-5.65 (m, 1H); MS: 258 (M+1).

Preparation of compound 20: Through the solution of compound 19 (32.1 g, 0.12 mol) in dichloromethane (300 mL) at −78° C. was bubbled ozone until the solution turned gray-blue. Then PPh$_3$ (50 g, 0.19 mol) was added slowly to quench the reaction. After concentration, the residue was purified by column chromatography on silica gel (PE: EA=10:1) to give compound 20 (22.1 g, 69.0%). $^1$H NMR (CDCl$_3$): δ0.78 (t, 3H), 1.51 (s, 9H), 1.65-1.69 (m, 1H, ), 2.15-2.35 (m, 1H), 2.91-2.96 (d, 1H,), 3.48-3.61 (m, 1H), 3.72 (s, 3H), 5.61 (br, 1H), 9.62 (s, 1H); MS: 260 (M+1).

Preparation of compound 21: To a solution of compound 20 (5.0 g, 19 mmol) in dichloromethane (50 mL) was added benzylamine (2.2 g, 21 mmol) and anhydrous MgSO$_4$ (6.8 g, 57 mmol). After stirring overnight, the resulting mixture was filtered and the filtrate was concentrated to afford compound 21 as a brown oil (6.7 g, 98.5%). $^1$H NMR (CDCl$_3$): δ0.78 (t, 3H), 1.51 (s, 9H), 1.65-1.69 (m, 1H, ), 2.15-2.35 (m, 1H), 2.86-2.96 (m, 1H), 3.2-3.3 (m, 1H), 3.65 (s, 3H), 4.55 (s, 2H), 5.61 (br, 1H), 7.21-7.41 (m, 5H), 7.31 (s, 1H).

Preparation of compound 22: To a solution of compound 21 (6.7 g, 18.9 mmol) in methanol (420 mL) was added NaBH$_4$ (3.5 g, 92.9 mmol). After stirring 3 h at room temperature, the mixture was poured into water, extracted with ethyl acetate, and the combined organic phases were dried over anhydrous Na$_2$SO$_4$ and concentrated to afford product 22 (5.3 g, 86.6%). $^1$H NMR (CDCl$_3$): δ0.88-0.93 (t, 3H), 1.43 (s, 9H), 1.65-1.71 (m, 2H, ), 2.25-2.55 (m, 2H), 3.10-3.31 (m, 2H), 4.40-4.45 (m, 1H), 4.51-4.62 (m, 1H), 5.2 (br, 1H), 7.23-7.36 (m, 5H); MS: 319 (M+1).

Preparation of compound 23: A solution of 22 (24.5 g, 77 mmol) in anhydrous HCl/CH$_3$OH (100 mL) was stirred for 3 h. Then the solvent was evaporated to afford the HCl salt of 23 (16 g, 95.3%). $^1$H NMR (CDCl$_3$): 0.82 (t, 3H), 1.52-1.63 (m, 2H), 1.71-1.83 (m, 1H), 2.05-2.10 (m, 1H), 2.20 (s, 2H), 3.01-3.21 (m, 2H), 4.28-4.56 (m, 2H), 7.17-7.35 (m, 5H); MS: 319 (M+1).

Preparation of compound 24: To a solution of LiAlH$_4$ (0.998 g, 26.2 mmol) in THF (10 mL) was added the solution of 23 (2.0 g, 7.87 mmol) in THF (20 ml) at room temperature. After stirring 2 h, water was added. The suspension was filtered through a pad of silica and the filtrate was evaporated. The residue was purified by column chromatography on silica gel (CH$_2$Cl$_2$: CH$_3$OH=10:1) to give compound 24 (0.9 g, 48%). $^1$H NMR (CDCl$_3$): 0.93-1.23 (t, 3H), 1.64-1.70 (m, 2H), 1.70-1.85 (m, 2H), 2.45-2.54 (m, 2H), 2.71-2.75 (m, 1H), 2.99-3.02 (m, 1H), 3.72 (s, 2H), 7.25-7.35 (m, 5H); MS: 205 (M+1).

Preparation of compound 25: To a solution of 24 (6.0 g, 0.029 mol) in methanol (50 mL) was added the solution of L-tartaric acid (5.2 g, 0.035 mol). After being stirred for 2 h, the resulting suspension was filtered and re-crystallized five times to get the desired compound 25 (2.3 g, 44.8%) as a white solid. $^1$H NMR (CDCl$_3$): 0.93-1.23 (t, 3H), 1.75-1.82 (m, 2H), 2.01-2.44 (m, 2H), 2.52-2.62 (m, 2H), 2.91-2.96 (d, 1H), 3.14-3.15 (m, 1H), 3.74-3.88 (m, 2H), 4.41 (s, 2H), 7.25-7.35 (m, 5H).

Preparation of the compound (+)-26: A solution of 25 (2.3 g, 9 mmol) in NaOH (2M) was stirred for 2 h at room temperature. The solution was extracted with ethyl acetate and the combined organic phases were dried over anhydrous Na$_2$SO$_4$ and concentrated to afford product (+)-26 (1.0 g, 98.7% ee) as a pale yellow solid.

Scheme 4: Synthesis of Compound (+)-32

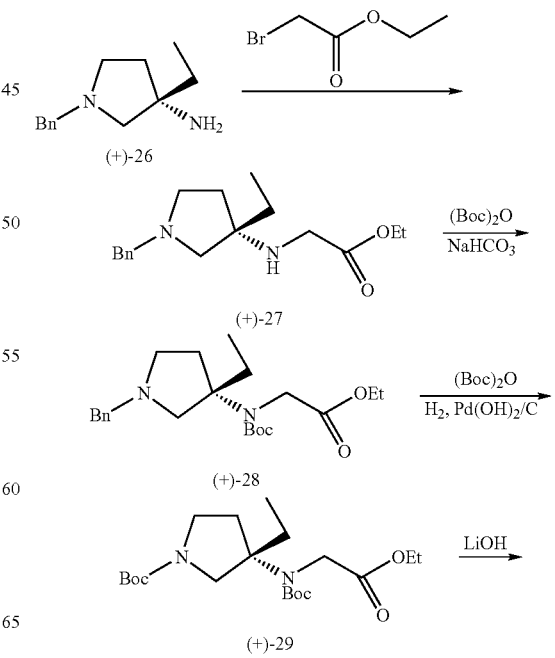

-continued

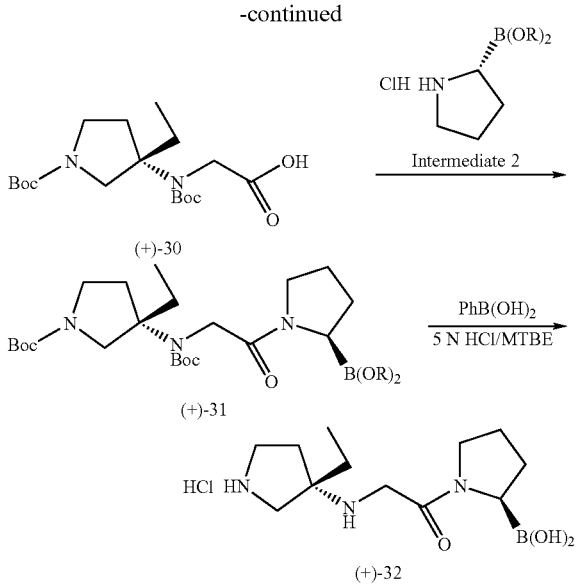

Preparation of compound (+)-27: To a solution of (+)-26 (1.14 g, 5.5 mmol) in THF (20 mL) at 0° C. was added ethyl bromoacetate (1.09 g, 6.6 mmol) and triethylamine (0.92 mL, 6.6 mmol). After stirring overnight, the precipitate was filtered off and the filtrate was concentrated to afford the crude product (+)-27 (1.61 g, 99%). MS: 291 (M+1).

Preparation of compound (+)-28: To a solution of (+)-27 (1.61 g, 5.5 mmol) in dichloromethane (15 mL) and sat. $NaHCO_3$ (15 mL) was added $(Boc)_2O$ (2.40 g, 11.0 mmol) and NaCl (2.0 g, 34 mmol) and heated to reflux overnight. After cooling to room temperature, water was added and the aqueous layer was extracted with chloroform. The combined organic layers were dried over anhydrous sodium sulfate and concentrated to give crude product (+)-28 (1.71 g, 80%). MS: 391 (M+1).

Preparation of compound (+)-29: The solution of (+)-28 (1.71 g, 4.4 mmol), $(Boc)_2O$ (1.9 g, 8.8 mmol) and palladium hydroxide on carbon (80 mg) in ethanol (40 mL) was hydrogenated at 40 psi for 3 hours. After the filtration to remove the catalyst, the filtrate was concentrated and the residue was purified by column chromatography on silica gel to give product (+)-29 (1.0 g, 57.0%). MS: 401 (M+1).

Preparation of compound (+)-30: To a solution of (+)-29 (500 mg, 1.25 mmol) in ethanol (10 mL) and water (2 mL) was added lithium hydroxide monohydrate (262 mg, 6.25 mmol) and the reaction was stirred for 2 hours. Then it was adjusted to pH 6 with 10% citric acid. The solution was extracted with ethyl acetate three times. The combined organic layers were dried over anhydrous sodium sulfate and concentrated to give compound (+)-30 (400 mg, 87%). MS: 373 (M+1).

Preparation of compound (+)-31: To a solution of compound (+)-30 (160 mg, 0.43 mmol) in dichloromethane (10 mL) at 0° C. was added N-methyl morpholine (219 μL, 1.57 mmol) and iso-butylchloroformate (70 mg, 0.52 mmol) under Ar atmosphere and stirred for 0.5 hours. Then Intermediate 2 (132 mg, 0.46 mmol) was added and the reaction was stirred for another 2 hours. Dichloromethane and sat. NaCl was added, and after the separation, the organic layer was washed with 6N HCl two times. Then the organic layer was dried over anhydrous sodium sulfate and concentrated to afford product (+)-31 (131 mg, 52%). MS: 590 (M+1).

Preparation of compound (+)-32: To a solution of compound (+)-31 (131 mg, 0.22 mmol) in MTBE (5 mL) and 5N HCl (5 mL) was added phenyl boronic acid (31.7 mg, 0.26 mmol) and stirred for 2 hours. Water was added and the resulting mixture was extracted with EA twice, dichloromethane twice, and then the aqueous layer was lyophilized to afford product (+)-32 (50 mg, 85%) (Table 1). $^1$H NMR (MeOD): δ1.07 (q, 3H), 1.70-1.80 (m, 1H), 1.95-2.10 (m, 5H), 2.35-2.52 (m, 2H), 3.15-3.23 (m, 1H), 3.44-3.82 (m, 4H), 3.95-4.15 (m, 2H). MS: 270 (M+1).

Scheme 5: Synthesis of Compound (-)-32

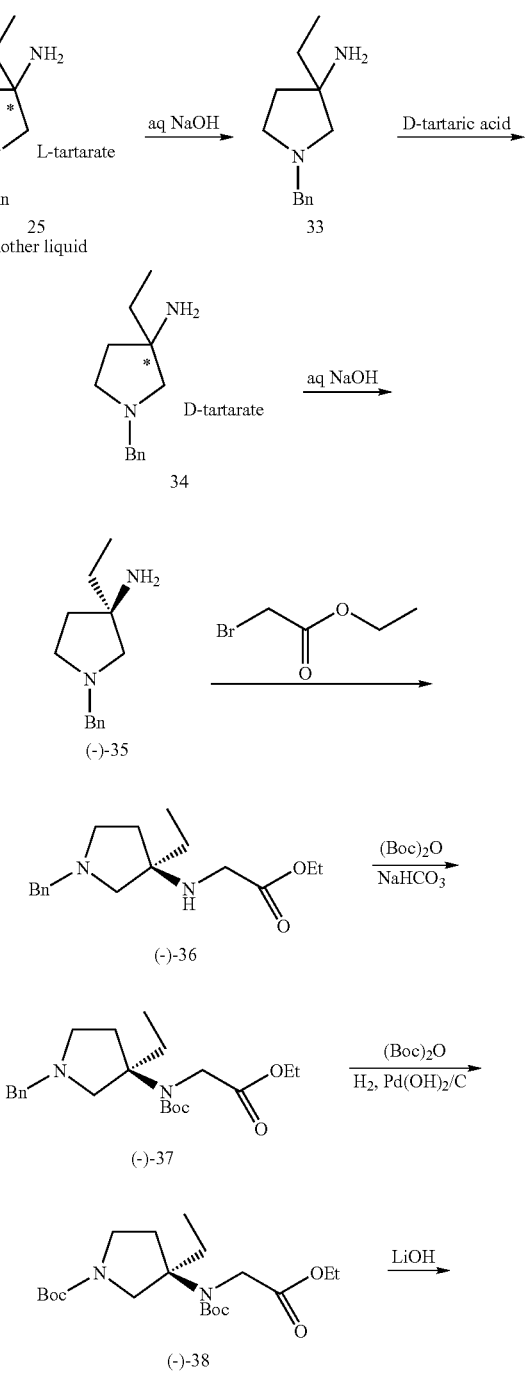

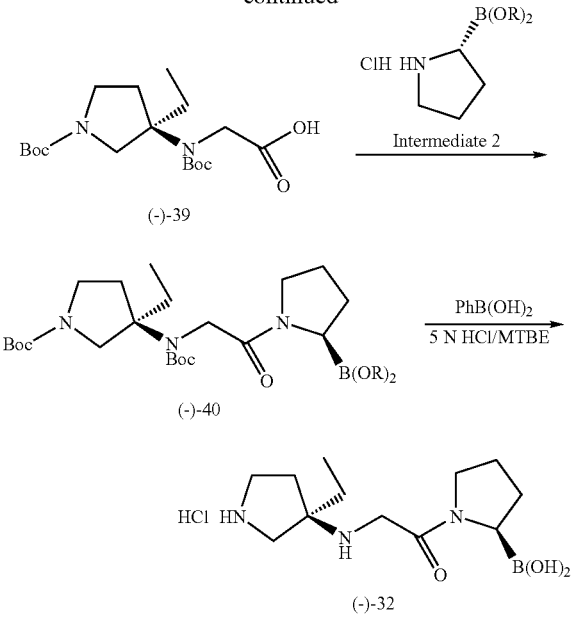

Preparation of compound 33: The mother liquor of 25 was stirred for 2 h at room temperature in 2N NaOH. The resulting solution was extracted with dichloromethane, and the combined organic phases were dried over anhydrous sodium sulfate and concentrated to afford product 33 (6.7 g).

Preparation of compound 34: To a solution of 33 (6.7 g, 33 mmol) in methanol (60 mL) was added the solution of D-tartaric acid (5.2 g, 0.035 mol). After being stirred for 2 h, the resulting suspension was filtered and re-crystallized five times to get the desired compound 34 (5 g, 87%) as a white solid. $^1$H NMR (CDCl$_3$): 1.0 (t, 3H), 1.79 (q, 2H), 2.01-2.10 (m, 2H), 2.52-2.62 (m, 2H), 2.95 (d, 1H), 3.11-3.16 (m, 1H), 3.73 (d, 1H), 3.60 (d, 1H), 4.42 (s, 2H), 7.25-7.40 (m, 5H).

Preparation of the compound (−)-35: The solution of 34 (5 g, 19 mmol) in NaOH (2M) was stirred for 2 h at room temperature. The resulting solution was extracted with ethyl acetate, and the combined organic phases were dried over anhydrous sodium sulfate and concentrated to afford product (−)-35 (2.0 g, 52%).

Preparation of compound (−)-36: To a solution of (−)-35 (1.5 g, 7.3 mmol) in THF (50 mL) at 0° C. was added ethyl bromoacetate (1.45 g, 8.7 mmol) and triethyl amine (1.22 mL, 47.1 mmol). After being stirred overnight, the precipitate was filtered out and the filtrate was concentrated to afford the crude product (−)-36 (1.98 g, 94%). MS: 291 (M+1).

Preparation of compound (−)-37: To a solution of (−)-36 (1.98 g, 6.8 mmol) in dichloromethane (25 mL) and sat. NaHCO$_3$ (25 mL) was added (Boc)$_2$O (2.96 g, 13.6 mmol) and NaCl (2.76 g, 47.2 mmol) and heated to reflux overnight. After cooling to room temperature, water was added and the aqueous layer was extracted with chloroform. The combined organic layers were dried over anhydrous sodium sulfate and concentrated to give crude product (−)-37 (2.3 g, 87%). MS: 391 (M+1).

Preparation of compound (−)-38: The solution of (−)-37 (2.3 g, 5.8 mmol), (Boc)$_2$O (2.52 g, 13.6 mmol) and palladium hydroxide on carbon (100 mg) in ethanol (40 mL) was hydrogenated at 40 psi for 3 hours. After the filtration to remove the catalyst, the filtrate was concentrated and the residue was purified by column chromatography on silica gel to give product (−)-38 (1.0 g, 43.0%). MS: 401 (M+1).

Preparation of compound (−)-39: To a solution of (−)-38 (500 mg, 1.25 mmol) in ethanol (10 mL) and water (2 mL) was added lithium hydroxide monohydrate (262 mg, 6.25 mmol) and the reaction was stirred for 2 hours. Then it was adjusted to PH 6 with 10% citric acid and extracted with EA for three times. The combined organic layers were dried over anhydrous sodium sulfate and concentrated to give compound (−)-39 (430 mg, 93%). MS: 373 (M+1).

Preparation of compound (−)-40: To a solution of compound (−)-39 (260 mg, 0.7 mmol) in dichloromethane (20 mL) at 0° C. was added N-methyl morpholine (316 mg, 3.13 mmol) and isobutylchloroformate (118 mg, 0.87 mmol) under Ar atmosphere and stirred for 0.5 hours. Then Intermediate 2 (214.5 mg, 0.75 mmol) was added and stirred for another 2 hours. Dichloromethane and sat. NaCl were added, and after the separation, the organic layer was washed with 6N HCl two times. The organic layer was dried over anhydrous sodium sulfate and concentrated to afford product (−)-40 (230 mg, 56%). MS: 590 (M+1).

Preparation of compound (−)-32: To a solution of compound (−)-40 (115 mg, 0.19 mmol) in MTBE (5 mL) and 5N HCl (5 mL) was added phenyl boronic acid (27.8 mg, 0.22 mmol) and stirred for 2 hours. Water was added and the resulting mixture was extracted with EA twice, dichloromethane twice, and then the aqueous layer was lyophilized to afford product (−)-32 (40 mg, 80%) (Table 1). $^1$H NMR (MeOD): δ1.05 (q, 3H), 1.90-2.05 (m, 6H), 2.28-2.35 (m, 2H), 3.15-3.20 (m, 1H), 3.44-3.62 (m, 4H), 3.90-4.00 (m, 2H). MS: 270 (M+1).

TABLE 1

| Compound No. | Name | Structure |
|---|---|---|
| 10 | (2R)-1-{2-[(3S)-Pyrrolidin-3-methyl-3-ylamino]-acetyl}-pyrrolidine-2-boronic acid | (+) - isomer |

TABLE 1-continued

| Compound No. | Name | Structure |
|---|---|---|
| 11 | (2R)-1-{2-[(3R)-Pyrrolidin-3-methyl-3-ylamino]-acetyl}-pyrrolidine-2-boronic acid | 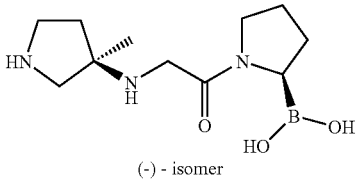<br>(−) - isomer |
| (+) 12 | (+)-(2R)-1-{2-[Pyrrolidin-3-ethyl-3-ylamino]-acetyl}-pyrrolidine-2-boronic acid | 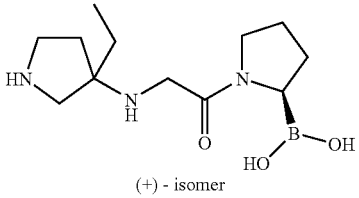<br>(+) - isomer |
| (−) 12 | (−)-(2R)-1-{2-[Pyrrolidin-3-ethyl-3-ylamino]-acetyl}-pyrrolidine-2-boronic acid | 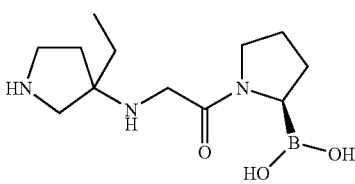<br>(−) - isomer |
| 13 | (2R)-1-{2-[Pyrrolidin-3-benzyl-3-ylamino]-acetyl}-pyrrolidine-2-boronic acid | 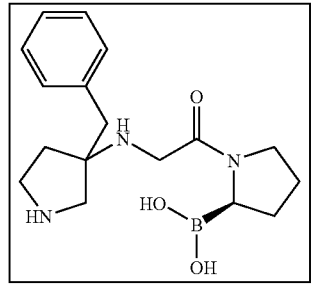 |

Example 3

Synthesis of Additional R-substituted Pyrrolidine Compounds

Using the procedures disclosed for examples 1 and 2, additional R-substituted pyrrolidine compounds can be prepared. To begin, the 2-amino, 2-R-substituted acetic acid ester starting material is used. The synthetic scheme is as follows. If an amine group is present in R, it is protected in a manner like that for protection of the left side pyrrolidine ring nitrogen depicted in scheme 6 and also as in Examples 1 and 2.

Scheme 6 - Synthesis of R-substituted Pyrrolidine Compounds

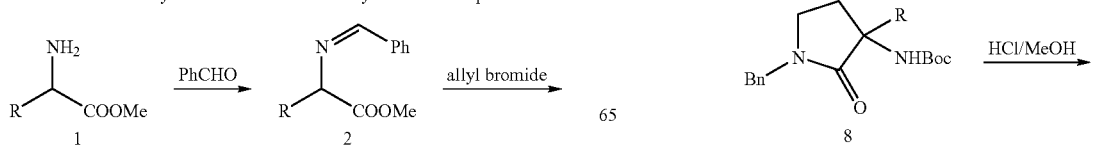

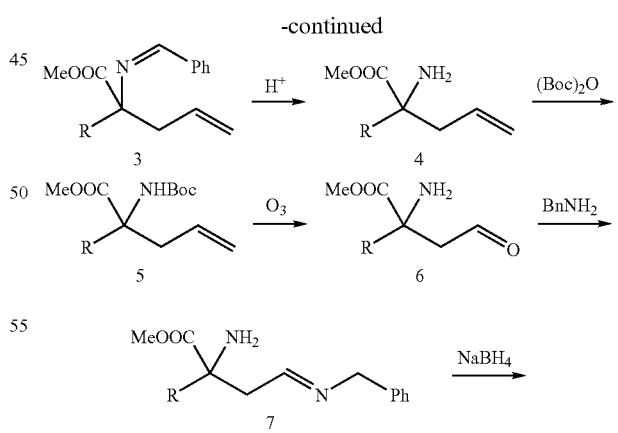

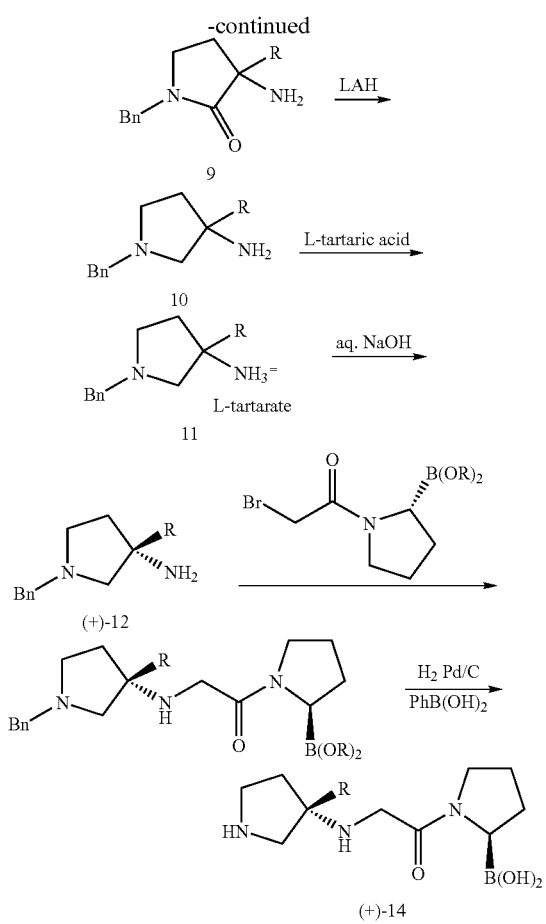

Example 4

DPP-IV Inhibitory Assays

The purification of porcine DPP-IV and the enzyme assay under steady state conditions are described in (1) Rahfeld, J. Schutkowski, M., Faust, J., Neubert., Barth, A., and Heins, J. (1991) Biol. Chem. Hoppe-Seyler, 372, 313-318; and (2) Nagatsu, T., Hino, M., Fuyamada, H., Hayakawa, T., Sakakibara, S., Nakagawa, Y., and Takemoto, T. (1976) Anal. Biochem., 74, 466-476, respectively. Human DPP-IV is also commercially available from, e.g., Research Diagnostics.

The activity of human DPP-IV was measured in vitro by its ability to cleave the synthetic substrate Gly-Pro-AMC. Cleavage of Gly-Pro-AMC by DPP-IV liberates the product AMC (7-amino-4-methyl coumarin), whose rate of appearance is directly proportional to the enzyme activity. Inhibition of the enzyme activity by specific enzyme inhibitors slows down the generation of AMC. Stronger interaction between an inhibitor and the enzyme results in a slower rate of generation of AMC. Thus, the degree of inhibition of the rate of accumulation of AMC is a direct measure of the strength of enzyme inhibition. The accumulation of AMC is measured fluorometrically. The $IC_{50}$ (concentration of test compound at which 50% of the enzyme activity is inhibited) for each compound is determined by incubating fixed amounts of enzyme with several different concentrations of inhibitor. The inhibition constant, $K_i$, can be determined for each compound by incubating fixed amounts of enzyme with several different concentrations of inhibitor and substrate.

The compounds of the invention were tested for their ability to inhibit the activity of purified DPP-IV using the following methods. DPP-IV enzyme activity was determined by a fluorometric assay with the substrate Gly-Pro-AMC which is cleaved by DPP-IV to release the fluorescent AMC leaving group. Free AMC (7-amino-4-methyl coumarin) was measured using an excitation wavelength of 380 nm and an emission wavelength of 460 nm with a Victor-II fluorescent reader. Stock solutions of DPP-IV (1 ng/μL, pH 8.0) and Gly-Pro-AMC substrate (400 μM) in 25 mM Tris buffer (pH 8.0) were prepared separately. Test compounds were dissolved in DMSO or in 50 mM glycine buffer (pH 3.0). The assay was performed by diluting the DPP-IV stock (10 μL) into 25 mM Tris buffer (77.5 μL) followed by addition of test compound (2.5 μL) at 26° C. After 10-minutes substrate was added (10 μL) and allowed to react for 20-minutes at 26° C. before free AMC was measured. $IC_{50}$ values were determined in triplicate, using a minimum of six different inhibitor concentrations. $IC_{50}$ values were calculated using Nonlinear Regression Analysis (GraphPad, Prism, San Diego, Calif.).

Compounds 10, 11, (+)-12, (−)-12 and 13 were tested in vitro as inhibitors of DPP-IV as described herein and each displayed an $IC_{50}$ of 1 μM or less.

Example 5

DPP-VII, DPP-VIII, DPP-IX, and FAP Inhibitory Assays

Recombinant DPP-VII, DPP-VIII, DPP-IX, and FAP enzymes were prepared as follows. The full length cDNAs for human DPP-VII, DPP-VIII, DPP-IX, and FAP were obtained from Open Biosystems. The cDNAs were cloned into the pFastBac vector with the addition of an N-terminal FLAG tag on DPP-VII, C-terminal 6xHis tags on DPP-VIII and DPP-IX, and an N-terminal 6xHis tag on FAP (Sun 2002, Qi 2003, and Chen 2004). Baculovirus was prepared using the Bac-to-Bac Baculovirus Expression System (Invitrogen). The cDNAs in the final baculovirus constructs were sequence verified.

To express the recombinant DPPs from the baculovirus constructs, S9 insect cells (cells and Sf-900 SFM media purchased from Invitrogen) were grown to mid log phase at 27° C. with shaking at 125 rpm and then adjusted to $2 \times 10^6$/mL just prior to baculovirus infection. Infection with DPP-VII, DPP-VIII, DPP-IX, and FAP baculoviral constructs were all performed at an MOI of 4. The infected cells were grown for 48 hours and the cell pellets harvested and frozen until purification. DPP-VII was purified using anti-FLAG immunoaffinity gel according to the manufacturer's instructions. DPP-VIII, DPP-IX, and FAP were purified using a B-PER 6xHis Fusion Protein Column Purification Kit from Pierce.

The activity of DPP-VII, DPP-VIII, DPP-IX and FAP was measured in vitro by its ability to cleave the synthetic substrates Lys-Pro AMC (DPP-VII) and Ala-Pro AMC (DPP-VIII, DPP-IX and FAP) (substrates purchased from Enzyme Systems). Recombinant DPPs were diluted in reaction buffer to give fluorescence values of 5000-20000 counts in the "enzyme only wells" 20 minutes after addition of substrate at 27° C. Reaction buffers were 25 mM (2-(4-Morpholino)-Ethane Sulfonic Acid), pH 5.5 for DPP-VII, 25 mM Tris, pH 8, 1% Triton X-l00, 100 mM NaCl for DPP-VIII, and 25 mM Tris pH 8 for DPP-IX and FAP. Test wells in a 96-well microtiter plate contained 88 μL of diluted DPP and 2.5 μL of titrated compound in 50 mM glycine, pH 2.6. "Enzyme only"

wells contained 88 μL of diluted DPP and 2.5 μL of glycine buffer. "No enzyme" wells contained 88 μL of reaction buffer without DPP and 2.5 μL of glycine buffer. All assays were done in triplicate. The plate was incubated at 27° C. for 10 minutes and then cooled on ice for 10 minutes. Ten microliters of substrate diluted in reaction buffer (40 μM final concentration) without Triton or NaCl were then added to all wells followed by incubation at 27° C. for 20 minutes. Fluorescence in each well was measured at settings of 380/460 nm. $IC_{50}$ calculations were performed by non-linear regression analysis using Prism software (GraphPad).

Example 6

DPP Selectivity of Boronic Acids

Using the methods described above, the DPP-IV, VII, VIII, IX and FAP inhibitory activities of compounds 10, 11, (+)-12, (−)-12 and 13, and the selectivity of compounds 10, 11, (+)-12, (−)-12 and 13 for DDP-IV, were compared to the closely related analogues shown in Table 2.

TABLE 2

Other Boronic Acid Inhibitors

| Compound No. | Structure | LC-MS |
|---|---|---|
| 5 | 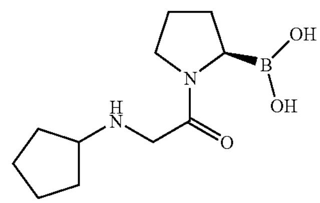 | |
| 14 | 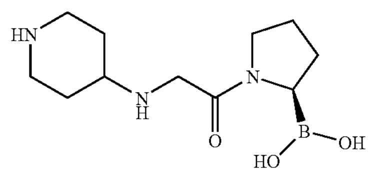 | 256(M + 1)(100) |
| 15 | 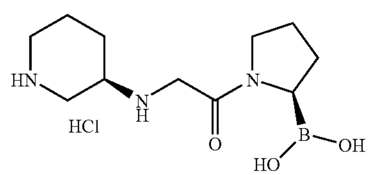 | 256(M + 1)(100), 238(8) |
| 16 | 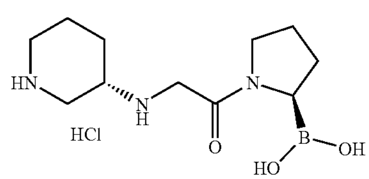 | 256(M + 1)(100), 238(10) |
| 17 | 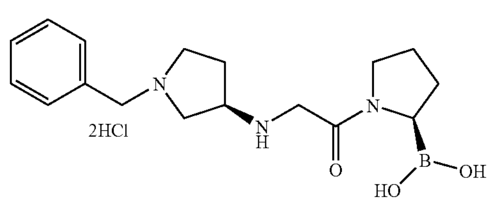 | 332(M + 1)(100), 314(10) |
| 18 | 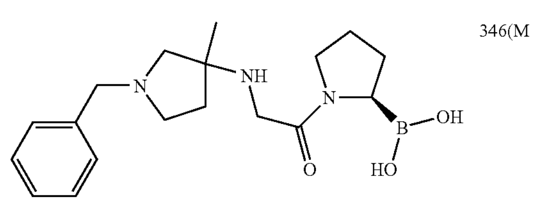 | 346(M + 1)(100), 328(12) |

TABLE 2-continued

Other Boronic Acid Inhibitors

| Compound No. | Structure | LC-MS |
|---|---|---|
| 19 | 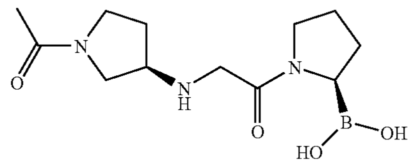 | 284(M + 1)(19), 266(100) |
| 20 | 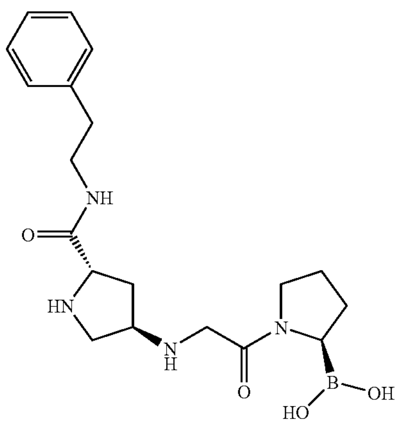 | 371(M − 17)major, 389(M + 1)minor |

The selectivity ratio value was obtained by dividing the $IC_{50}$ value for DPP-VII, DPP-VIII, DPP-IX or FAP by the $IC_{50}$ value for DPP-IV and assigned a selectivity ratio defined as $A \leq 1$; $1 < B \leq 10$; $10 < C \leq 50$; $D > 50$. Results are summarized in Table 3.

TABLE 3

DPP Selectivity Ratios

| | Selectivity Ratios* | | | |
|---|---|---|---|---|
| Compound No. | DPP-VII | DPP-VIII | DPP-IX | FAP |
| 5 | A | B | A | B |
| 10 | D | D | C | D |
| 11 | C | D | C | D |
| (+)-12 | D | D | C | D |
| (−)-12 | B | C | B | D |
| 13 | D | D | C | D |
| 14 | A | B | A | D |
| 15 | A | B | A | C |
| 16 | B | C | A | C |
| 17 | B | B | A | C |
| 18 | B | C | A | C |
| 19 | A | B | B | B |
| 20 | A | A | A | B |

*Selectivity ratios:
$A \leq 1$;
$1 < B \leq 10$;
$10 < C \leq 50$;
$D > 50$

The claimed compounds, e.g. compounds 10, 11, (+)-12, (−)-12, and 13 showed greatly improved selectivity in contrast to their closely related analogues. For example, compound 10 showed excellent selectivity for DPP-IV relative to DPP-VIII. Replacement of the 3-aminopyrrolidine with cyclopentyl 5, 4-piperidinyl 14, 3R-piperidinyl 15, or 3S-piperidinyl 16 (Table 2) maintains inhibition of DPP-IV. However, compounds 5, 14, 15, and 16 are significantly less selective towards the other dipeptidyl peptidases with one or more exhibiting selectivity ratios $\leq 1$; and two or more exhibiting selectivity ratios $\leq 10$. Thus, examples of the claimed compounds demonstrate unexpected selectivity towards the other dipeptidyl peptidases while maintaining potency against DPP-IV, while the close structural analogues of the selective compounds of the invention exhibit significant activity against one or more of the other dipeptidyl peptidases.

Also, addition of further moieties at positions on the pyrrolidine ring produces compounds with reduced selectivity towards the other dipeptidyl peptidases. Alkylation of the pyrrolidine nitrogen yielding compounds 17 and 18, acylation of the pyrrolidine nitrogen yielding compound 19 or incorporation of a carboxamide yielding compound 20 all lead to a substantial loss of selectivity. See Table 2 for the structures of these compounds.

While the invention has been described and exemplified in sufficient detail for those skilled in this art to make and use it, various alternatives, modifications, and improvements will be apparent to those skilled in the art without departing from the spirit and scope of the claims.

All patents and publications are herein incorporated by reference to the same extent as if each individual publication was specifically and individually indicated to be incorporated by reference.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A pyrrolidine compound represented by formula I:

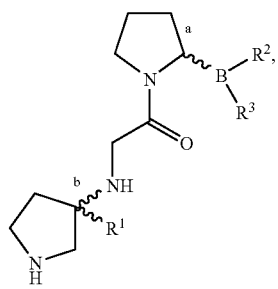

(I)

a cyclic isomer thereof wherein the cyclic isomer is a compound of formula (V):

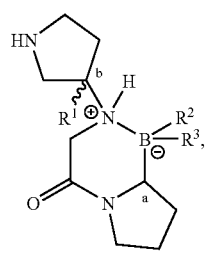

(V)

wherein the asymmetric carbons $C^a$ and $C^b$ independently have an R configuration, an S configuration, or a mixture of both configurations such that all stereoisomers and all stereomeric mixtures are included, any pharmaceutically acceptable salt thereof, or any prodrug thereof;

wherein, $R^1$ is a substituted or unsubstituted $(C_{3-8})$ alkyl, alkenyl, aralkyl, cycloalkyl, cycloalkylalkyl, cycloalkenyl, cycloalkenylalkyl, heterocyclyl, or heterocyclylalkyl group;

$R^2$ and $R^3$, independently or together, are —OH, —O⁻ M⁺ wherein M⁺ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$ independently indicate for each asymmetric carbon an R configuration, an S configuration, or a mixture of both configurations such that all stereoisomers and all stereomeric mixtures are included.

2. A pyrrolidine compound of claim 1 having an R configuration at $C^a$.

3. The pyrrolidine compound of claim 2 having an R configuration at $C^b$.

4. The pyrrolidine compound of claim 2 having an S configuration at $C^b$.

5. An optically-enriched stereoisomer of the pyrrolidine compound of claim 1.

6. A stereomeric mixture of two or more stereoisomers of the pyrrolidine compound of claim 1, wherein at least one of the asymmetric carbons, $C^a$ or $C^b$, has both R and S configurations.

7. A stereomeric mixture of claim 6, which is a mixture of two diastereoisomers, an enantiomeric pair, a racemic mixture, a mixture of an enantiomeric pair plus a diastereomer, or an optically active mixture of at least two stereoisomers.

8. A stereomeric mixture of claim 6, wherein one stereoisomer predominates and the predominant isomer has an R configuration at $C^a$ and an R or S configuration at $C^b$.

9. A stereomeric mixture of claim 8, wherein the predominant isomer has an R configuration at $C^b$.

10. A stereomeric mixture of claim 6, wherein two optical isomers predominate, one having R configurations at $C^a$ and $C^b$, and one having an R configuration at $C^a$ and an S configuration at $C^b$.

11. The pyrrolidine compound of claim 1, wherein $R^1$ is a substituted or unsubstituted $(C_{3-8})$alkyl or $(C_{3-12})$cycloalkyl group; or is a $(C_{1-4}$ alkyl)phenyl or phenyl group, wherein the $(C_{1-4}$ alkyl)phenyl and phenyl, groups are optionally mono- or independently di-substituted with $R^4$; and wherein, $R^4$ is halogen, trifluoromethyl, cyano, nitro, $(C_{1-6})$alkyl, $(C_{1-6})$alkoxy, cycloalkyl, carboxy, acetamido, hydroxyl, hydroxy$(C_{1-6})$alkyl, hydroxymethyl, trifluoromethoxy, amido, carbamyl, sulfonamide, alkylsulfonyl, phenylsulfonyl, aryl, heteroaryl, wherein the aryl and heteroaryl groups are optionally substituted with one or more $R^5$; and $R^5$ is halogen, $(C_{1-6})$alkyl, $(C_{1-6})$alkoxy, $(C_{1-6})$alkylamino, $(C_{1-10})$ dialkylamino, benzyl, benzyloxy, hydroxyl$(C_{1-6})$alkyl, hydroxymethyl, nitro, trifluoromethyl, trifluoromethoxy, trifluoromethylthio, N-hydroxyimino, cyano, carboxy, acetamido, hydroxyl, sulfonamide, or carbamyl.

12. The pyrrolidine compound of claim 1, wherein $R^1$ is a substituted or unsubstituted $(C_{3-6})$alkyl or $(C_{1-4}$ alkyl)phenyl group.

13. The pyrrolidine compound of claim 1, wherein $R^1$ is propyl, butyl, isopropyl, isobutyl, cyclopentyl, t-butyl or benzyl.

14. The pyrrolidine compound of claim 1, wherein $R^2$ and $R^3$ are independently hydroxyl, methoxy, ethoxy, n-propoxy, i-propoxy, or n-butoxy; or together are 1,2-dioxaethylene, 1,3-dioxapropylene, or pinanedioxy.

15. The pyrrolidine compound of claim 1, wherein $R^2$ and $R^3$ are both hydroxyl.

16. The pyrrolidine compound of claim 1 selected from the group consisting of (2R)-1-{2-[(3S)-Pyrrolidin-3-propyl-3-ylamino]-acetyl}-pyrrolidine-2-boronic acid, (2R)- 1- {2-[(3R)-Pyrrolidin-3-propyl-3-ylamino]-acetyl}-pyrrolidine-2-boronic acid, (2R)- 1- {2-[(3S) -Pyrrolidin-3-benzyl-3-ylamino]-acetyl}-pyrrolidine-2-boronic acid, (2R)-1-{2-[(3R) -Pyrrolidin-3-benzyl-3-ylamino]-acetyl}-pyrrolidine-2-boronic acid.

17. A pyrrolidine compound of claim 1 having the structure:

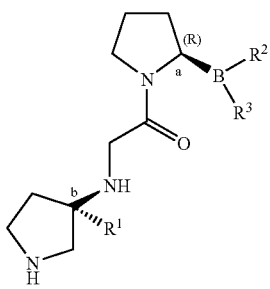

and having a stereomeric purity of at least about 55%.

18. A pyrrolidine compound of claim 17 having a stereomeric purity of at least about 90%.

19. A pyrrolidine compound of claim 17 having a stereomeric purity of at least about 98%.

20. A pyrrolidine compound of claim 1 having the structure:

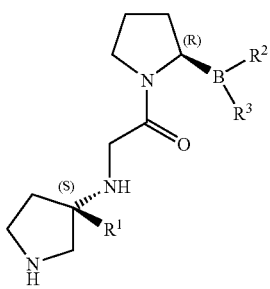

and having a stereomeric purity of at least about 55%.

21. A pyrrolidine compound of claim 20 having a stereomeric purity of at least about 90%.

22. A pyrrolidine compound of claim 20 having a stereomeric purity of at least about 98%.

23. A pharmaceutical combination comprising:
a pyrrolidine compound represented by formula I:

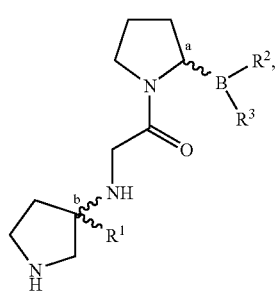

a cyclic isomer thereof wherein the cyclic isomer is a compound of formula (V):

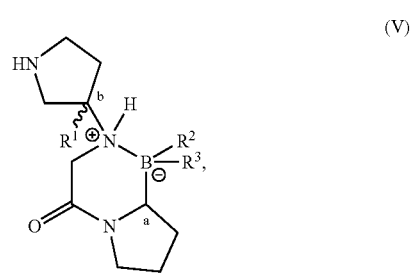

wherein the asymmetric carbons $C^a$ and $C^b$ independently have an R configuration, an S configuration, or a mixture of both configurations such that all stereoisomers and all stereomeric mixtures are included, any pharmaceutically acceptable salt thereof, or any prodrug thereof; wherein, $R^1$ is a substituted or unsubstituted $(C_{3-8})$ alkyl, $(C_{2-8})$ alkenyl, $(C_6\text{-}C_{15})$ aralkyl, $(C_3\text{-}C_{12})$ cycloalkyl, $(C_4\text{-}C_{20})$ cycloalkylalkyl, $(C_3\text{-}C_{12})$cycloalkenyl, $(C_4\text{-}C_{20})$ cycloalkenylalkyl, $(C_3\text{-}C_{20}$ with N, O and/or S) heterocyclyl, or $(C_4\text{-}C_{20}$ with N, O and/or S) heterocyclylalkyl group;

$R^2$ and $R^3$ independently or together are —OH, —O⁻ M⁺ wherein M⁺ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$ independently indicate for each asymmetric carbon an R configuration, an S configuration, or a mixture of both configurations such that all stereoisomers and all stereomeric mixtures are included; and a known second medicament that increases insulin secretion, increases insulin sensitivity, reduces the uptake of sugar from the gastrointestinal track, enhances the effect of endogenous peptides or proteins that affect glycemic control, provides a replacement for endogenous peptides or proteins that affect glycemic control, or any combination thereof.

24. A pharmaceutical combination of claim 23, wherein the second medicament is an antidiabetic agent.

25. A pharmaceutical combination of claim 24, wherein the weight ratio of the compound of formula I and the antidiabetic agent is from about 0.01:1 to about 100:1.

26. A pharmaceutical combination of claim 23, wherein the second medicament is glyburide, glipizide, nateglinide, repaglinide, metformin, pioglitazone, rosiglitazone, acarbose, miglitol, exenatide, insulin, or any combination thereof.

27. A pharmaceutical combination of claim 23, wherein the second medicament is suitable for treatment of a diabetes-associated condition.

28. A pharmaceutical composition comprising:
a pyrrolidine compound represented by formula I:

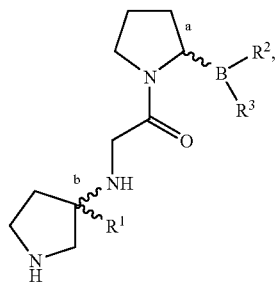

(I)

or a cyclic isomer thereof wherein the cyclic isomer is a compound of formula (V):

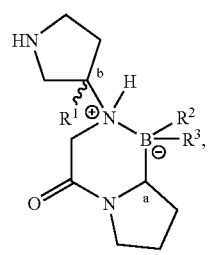

(V)

wherein the asymmetric carbons $C^a$ and $C^b$ independently have an R configuration, an S configuration, or a mixture of both configurations such that all stereoisomers and all stereomeric mixtures are included, or any pharmaceutically acceptable salt thereof, or any prodrug thereof; wherein, $R^1$ is a substituted or unsubstituted $(C_{3-8})$alkyl,$(C_{2-8})$alkenyl,$(C_6-C_{15})$aralkyl, $(C_3-C_{12})$ cycloalkyl, $(C_4-C_{20})$ cycloalkylalkyl, $(C_3-C_{12})$ cycloalkenyl, $(C_4-C_{20})$ cycloalkenylalkyl, $(C_3-C_{20}$ with N, O and/or S) heterocyclyl, or $(C_4-C_{20}$ with N, O and/or S) heterocyclylalkyl group;

$R^2$ and $R^3$, independently or together, are —OH, —O$^-$ M$^+$ wherein M$^+$ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$ independently indicate for each asymmetric carbon an R configuration, an S configuration, or a mixture of both configurations such that all stereoisomers and all stereomeric mixtures are included; and (b) a pharmaceutically acceptable carrier.

29. A pharmaceutical composition of claim 28, further comprising (c) a second medicament selected from the group consisting of a known second medicament that increases insulin secretion, increases insulin sensitivity, reduces the uptake of sugar from the gastrointestinal track, enhances the effect of endogenous peptides or proteins that affect glycemic control, or provides a replacement for endogenous peptides, proteins that affect glycemic control, or any combination thereof.

30. A process for manufacture of a pharmaceutical composition of claim 28 comprising combining a pyrrolidine compound with a pharmaceutically acceptable carrier or diluent.

31. The process of claim 30, wherein the pharmaceutically acceptable carrier or diluent is suitable for oral administration or parenteral administration.

32. The process of claim 30, further comprising the step of formulating the composition into a tablet or capsule.

33. The process of claim 30, further comprising the step of lyophilizing the composition or the compound of formula I.

34. A method for inhibiting dipeptidyl peptidase-IV comprising contacting dipeptidyl peptidase-IV with an effective amount of a pyrrolidine compound represented by formula I:

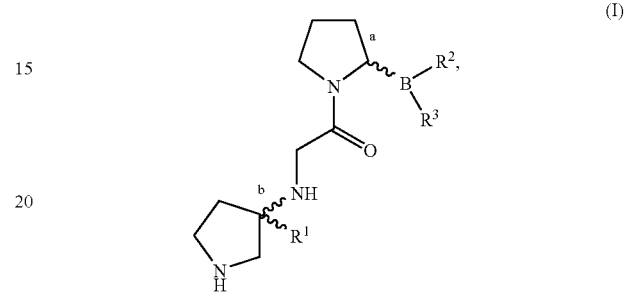

(I)

a cyclic isomer thereof wherein the cyclic isomer is a compound of formula (V):

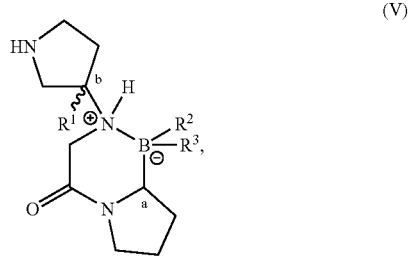

(V)

wherein the asymmetric carbons $C^a$ and $C^b$ independently have an R configuration, an S configuration, or a mixture of both configurations such that all stereoisomers and all stereomenc mixtures are included, any pharmaceutically acceptable salt thereof, or any prodrug thereof; wherein, $R_1$ is a substituted or unsubstituted $(C_{3-8})$ alkyl, $(C_{2-8})$ alkenyl, $(C_6-C_{15})$ aralkyl, $(C_3-C_{12})$ cycloalkyl, $(C_4-C_{20})$ cycloalkylalkyl, $(C_3-C_{12})$ cycloalkenyl, $(C_4-C_{20})$ cycloalkenylalkyl, $(C_3-C_{20}$ with N, O and/or S) heterocyclyl, or $(C_4-C_{20}$ with N, O and/or S) heterocyclylalkyl group;

$R^2$ and $R^3$, independently or together, are —OH, —O$^-$ M$^+$ wherein M$^+$ is a cation, a hydroxyl bearing a boronic acid protecting group, or a group capable of being hydrolyzed to a hydroxyl group in an aqueous solution at physiological pH or in biological fluids; and the wavy lines at asymmetric carbons $C^a$ and $C^b$ independently indicate for each asymmetric carbon an R configuration, an S configuration, or a mixture of both configurations such that all stereoisomers and all stereomeric mixtures are included.

35. A method according to claim 34, wherein the dipeptidyl peptidase-IV is within a mammal in need of treatment for a malcondition selected from diabetes or errors in glucose metabolism, and the contacting step comprises administering to the mammal a therapeutically effective amount of a compound of formula I.

36. The method of claim 35, wherein the malcondition is impaired glycemic control.

37. The method of claim 35, wherein the malcondition is diabetes.

38. The method of claim 35, further comprising administering a therapeutically effective amount of a second medicament selected from the group consisting of a known second medicament that increases insulin secretion, increases insulin sensitivity, reduces the uptake of sugar from the gastrointestinal track, enhances the effect of endogenous peptides or proteins that affect glycemic control, or provides a replacement for endogenous peptides, proteins that affect glycemic control, or any combination thereof.

39. The method of claim 34, wherein the pyrrolidine compound selectively inhibits dipeptidyl peptidase-IV over at least one other dipeptidyl peptidase.

40. The method of claim 39, wherein the selective inhibition is by greater than 5-fold.

41. The method of claim 39, wherein the pyrrolidine compound selectively inhibits dipeptidyl peptidase-IV over dipeptidyl peptidase-VII, dipeptidyl peptidase-VIII, dipeptidyl peptidase-IX or fibroblast activation protein.

42. The method of claim 39, wherein the pyrrolidine compound selectively inhibits dipeptidyl peptidase-IV over dipeptidyl peptidase-VIII by greater than 10-fold.

43. The method of claim 39, wherein the pyrrolidine compound selectively inhibits dipeptidyl peptidase-IV over dipeptidyl peptidase-VIII and fibroblast activation protein.

44. The method of claim 39, wherein the pyrrolidine compound selectively inhibits dipeptidyl peptidase-IV over dipeptidyl peptidase-VII, dipeptidyl peptidase-VIII, and fibroblast activation protein.

45. A process for preparing an intermediate of formula IV:

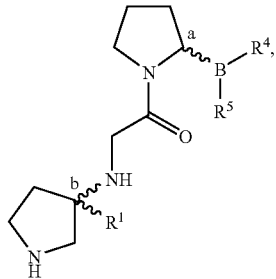

(IV)

comprising contacting an intermediate of formula II:

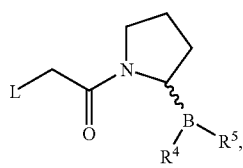

(II)

with an amine of formula III:

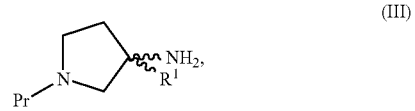

(III)

wherein L is a leaving group, $R^1$ is a substituted or unsubstituted $(C_{3-8})$ alkyl, $(C_{2-8})$ alkenyl, $(C_6-C_{15})$ aralkyl, $(C_3-C_{12})$ cycloalkyl, $(C_4-C_{20})$ cycloalkylalkyl, $(C_3-C_{12})$ cycloalkenyl, $(C_4-C_{20})$ cycloalkenylalkyl, $(C_3-C_{20}$ with N, O and/or S) heterocyclyl, or $(C_4-C_{20}$ with N, O and/or S) heterocyclylalkyl group, and $R^4$ and $R^5$ are, independently or together, groups that can be converted to hydroxyl, and the wavy lines at the asymmetric carbons $C^a$ and $C^b$ independently indicate for each asymmetric carbon an R configuration, an S configuration, or a mixture of both configurations such that all stereoisomers and all stereomeric mixtures are included, and Pr is an N-protecting group.

46. The process of claim 45, wherein L is a halogen, mesylate, tosylate or triflate, and Pr is Boc, Cbz, Fmoc, or benzyl.

47. The process of claim 45, wherein the absolute configuration at $C^a$ is R, and the absolute configuration at $C^b$ is R or S.

48. A process for preparing a pyrrolidine compound represented by formula I and the cyclic isomer thereof:

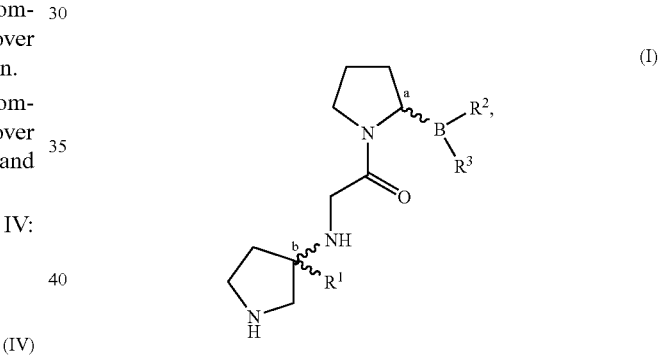

(I)

wherein the cyclic isomer is a compound of formula (V):

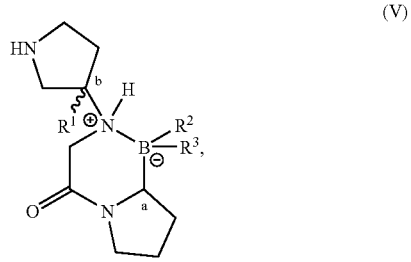

(V)

wherein the asymmetric carbons $C^a$ and $C^b$ independently have an R configuration, an S configuration, or a mixture of both configurations such that all stereoisomers and all stereomeric mixtures are included, comprising converting the Pr group of intermediate IV of claim 45 to hydrogen to form a pyrrolidine compound of formula I wherein $R^2$ and $R^3$ are equivalent to $R^4$ and $R^5$ of claim 45 respectively, and the wavy lines at the asymmetric carbons $C^a$ and $C^b$ independently indicate for each asymmetric carbon an R configuration, an S configuration, or a mixture of both configurations such that all stereoisomers and all stereomeric mixtures are included, and Pr is an N-protecting group.

49. A process of claim 48, further comprising converting $R^4$ and $R^5$ to hydroxyl such that $R^2$ and $R^3$ are both hydroxyl.

50. The process of claim 49, wherein the pyrrolidine compound is a mixture of stereoisomers.

51. The process of claim 49 wherein one or two of the stereoisomers predominate and those stereoisomers have an R configuration at $C^a$ and an R or S configuration $C^b$.

52. The process of claim 45, further comprising resolving the intermediate of formula IV to produce at least a stereomeric mixture in which one or two stereoisomers predominate.

53. The process of claim 48, further comprising resolving the pyrrolidine compound to produce at least a stereomeric mixture in which one or two stereoisomers predominate.

54. A pyrrolidine compound of claim 1, wherein $R^2$ and $R^3$ independently or together are the boronic acid protecting group formed from (+)-pinanediol; pinacol; 1,2-dicyclohexyl-ethanediol; 1,2-ethanediol; 2,2-diethanolamine; 1,3-propanediol; 2,3-butanediol, diisopropyl tartrate; 1,4-butanediol; diisopropylethanediol; (S,S,)-5,6-decanediol; 1,1,2-triphenyl-1,2-ethanediol; (2R,3R)-1,4-dimethyoxy-1,1,4,4-tetraphenyl-2,3-butanediol; methanol; ethanol; isopropanol; catechol; or 1-butanol.

55. The pyrrolidine compound of claim 1, wherein $R^2$ and $R^3$ are both hydroxyl.

56. The pyrrolidine compound of claim 1, wherein $R^1$ is a substituted or unsubstituted ($C_{3-8}$) alkyl, ($C_{2-8}$) alkenyl, ($C_6$-$C_{15}$) aralkyl, ($C_3$-$C_{12}$) cycloalkyl, ($C_4$-$C_{20}$) cycloalkylalkyl, ($C_3$-$C_{12}$) cycloalkenyl, ($C_4$-$C_{20}$) cycloalkenylalkyl, ($C_3$-$C_{20}$ with N, O and/or S) heterocyclyl, or ($C_4$-$C_{20}$ with N, O and/or S) heterocyclylalkyl group.

* * * * *